(12) United States Patent
Rane et al.

(10) Patent No.: US 9,321,782 B2
(45) Date of Patent: Apr. 26, 2016

(54) PROCESS FOR PREPARATION OF NOVEL 42-O-(HETEROALKOXYALKYL) RAPAMICIN COMPOUNDS WITH ANTI-PROLIFERATIVE PROPERTIES

(75) Inventors: Dhananjay Sharad Rane, Thane (IN); Rajnikant Gandalal Vyas, Mumbai (IN); Pramod Kumar Minocha, Gujarat (IN)

(73) Assignee: MERIL LIFE SCIENCES PVT. LTD., Gujarat (IN)

( * ) Notice: Subject to any disclaimer, the term of this patent is extended or adjusted under 35 U.S.C. 154(b) by 447 days.

(21) Appl. No.: 13/814,174

(22) PCT Filed: Aug. 2, 2011

(86) PCT No.: PCT/IN2011/000508
§ 371 (c)(1),
(2), (4) Date: Feb. 26, 2013

(87) PCT Pub. No.: WO2012/017449
PCT Pub. Date: Feb. 9, 2012

(65) Prior Publication Data
US 2013/0184305 A1    Jul. 18, 2013

(30) Foreign Application Priority Data
Aug. 4, 2010   (IN) .......................... 299/MUM/2010

(51) Int. Cl.
| A61K 31/44 | (2006.01) |
| C07D 491/18 | (2006.01) |
| A61K 31/436 | (2006.01) |
| C07D 498/18 | (2006.01) |
| A61M 25/10 | (2013.01) |

(52) U.S. Cl.
CPC ............ C07D 491/18 (2013.01); A61K 31/436 (2013.01); A61M 25/10 (2013.01); C07D 498/18 (2013.01)

(58) Field of Classification Search
CPC ... A61K 31/44; A61K 31/436; C07D 491/18; C07D 498/18; A61M 25/10
USPC .......................... 514/291; 604/103.02; 546/90
See application file for complete search history.

(56) References Cited

U.S. PATENT DOCUMENTS
| 5,151,413 A | 9/1992 | Caufield et al. |
| 5,362,718 A | 11/1994 | Skotnicki et al. |
| 2005/0101624 A1 | 5/2005 | Betts et al. |

FOREIGN PATENT DOCUMENTS
| EP | 1826211 A | 8/2007 |
| WO | 0187382 A | 11/2001 |

OTHER PUBLICATIONS

International Search Report dated Dec. 28, 2011 for PCT/IN2011/000508.
International Preliminary Report on Patentability Nov. 5, 2012 for PCT/IN2011/000508.

*Primary Examiner* — Jason Sims
*Assistant Examiner* — Ibrahim D Bori
(74) *Attorney, Agent, or Firm* — Kramer & Amado, P.C.

(57) ABSTRACT

The invention discloses novel 42-0-(heteroalkoxyalkyl) rapamycin compounds of formula (1) and process for preparation thereof. These compounds are useful in the treatment of hyperproliferative vascular diseases such as restenosis and atherosclerosis Wherein, R denotes 3, 4 and 5 membered 3-hydroxy heteroalkoxyalkyl compounds selected from Tetrahydrofuran-3-ol, Oxetan-3-ol, Tetrahydropyran-3-ol, Tetrahydro-4- methyl furan-3-ol, Tetrahydro-2,5,5-trimethyl furan-3-ol, Tetrahydro-2,5-diethyl-2-methyl furan-3-ol, Tetrahydro-6-methoxy-2-methyl 2H-Pyran-3-ol and Tetrahydro-2,2-dimethyl-6-phenyl 2H-Pyran-3-ol.

(1)

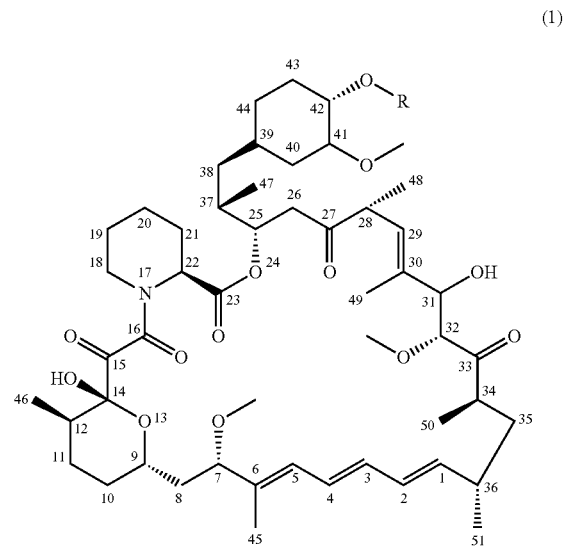

16 Claims, 4 Drawing Sheets

PROCESS FOR PREPARATION OF NOVEL 42-O-(HETEROALKOXYALKYL) RAPAMICIN COMPOUNDS WITH ANTI-PROLIFERATIVE PROPERTIES

FIELD OF THE INVENTION

This invention is directed to novel 42-O-(heteroalkoxyalkyl) rapamycins as well as their methods for making, their biocompatibility and anti-proliferative properties.

BACKGROUND OF THE INVENTION

On reviewing of literature on rapamycin and some of its derivatives; specifically used for controlling restenosis treatment, we found that the control of the restenosis after percutaneous transluminal coronary angioplasty (PTCA) still remains one of the most important limitations. Despite of early success, the occurrence of restenosis after initial PTCA is between 30 and 50%, however later years it is reduced to 20-30%, (Hamon, M. et al., Drug Therapy, 4: 291-301 (1998); Bauters C. et al., European Heart Journal, 16: 3348 (1995)). Neo-intimal hyperplasia and vascular remodelling are two major component processes considered for restenosis after PTCA, the former coming initially, the latter occurring later in the process (Hoffman, R. et al., Circulation, 94: 1247-1254 (1996); Oesterle, S. et al., American Heart Journal, 136: 578-599 (1998), Kenneth G. et al., Journal of the American collage of cardiology, 35: 583-591 (2000)).

With use of vascular remodelling process control approach, one should eliminate or reduce restenosis. This can be skilfully done by implanting a metal stent in the stenosed lumen of the arterial vessel after PTCA procedure. Coronary stents are tiny tubular scaffolds which are widely used to prevent acute reclosure or collapse of weakened vessels following angioplasty procedure. Stents are now regularly implanted in 70 to 80% of all interventional cases (Emanuele B. et Al., European Heart Journal, 24: 394-403 (2003), Schluter L. et al., Kardiovask Med., 7: 61-70 (2005).

Despite of this success, the problem of restenosis is yet to be completely understood or conquered (Hamon, M. et al., Drug Therapy, 4: 291-301 (1998); Oesterle, S. et al., American Heart Journal, 136: 578-599 (1998)) The injury in target vessel during balloon angioplasty and stent implantation procedure often induce excessive healing response, including thrombosis and cell proliferation, which eventually leads to the in-stent restenosis. There remains a need to solve the eventual renarrowing of the lumen inside the stent (i.e. restenosis) after angioplasty and stent placement experienced by many patients ((Lally C. et al., .Wiley Encyclopedia of Biomedial Engineering 2006); (Peter J. et at., Rev. Esp. Cardiol. 61: 1001-1006 (2008)).

This problem is addressed by the use of antiproliferative drugs like paclitaxel, rapamycin and its analogues as mentioned in various publications. The family of paclitaxel drug in general has cytotoxic properties hence it has limited application in the use of drug eluting stents. On the other hand drug rapamycin and its analogues are widely used for this application being non-cytotoxic (cytostatic) in nature.

In an effort to increase the potency or specificity of pharmacological action till date various structural features of rapamycin have been modified. We found number of U.S. patents such as U.S. Pat. No. 7,220,755 discloses 42-O-alkoxyalkyl rapamycin derivatives and composition comprising same, U.S. Patent. No. 2009/0209572 discloses 36-DES (3-Methoxy-4-Hydroxycyclohexyl) 36-(3-Hydroxycycloheptyl) derivatives of rapamycin, U.S. Pat. No. 7,812,155 B2 discloses process for preparing an O-alkylated Rapamycin derivatives having normal stereochemistry at the 42 position. The PCI published application 2010/0249415 A1 discloses process for preparation of Temsirolimus.

Some chemical modifications of rapamycin have been attempted in recent years. These include the preparation of O-alkylated rapamycin derivatives by Masashi Isozaki in U.S. Pat. No. 7,193,078 B2, March 2007; Pimecrolimus a rapamycin derivative by Viktor Gyollai in U.S. Pat. No. 7,279,571 B2, Oct. 2007; Tetrazole derivatives of rapamycin by Madhup Dhaon in U.S. Patent 2010/0204466 A1, August 2010 and Alkyl benzene sulfonate rapamycin derivatives by Kwang-Chung Lee in U.S. Pat. No. 7,872,122 B2, January 2011. However, these attempts were limited to manufacturing process and no further potency study of these derivatives completed. Therefore, there remains unmet need for rapamycin derivatives with improved anti-proliferative properties.

Accordingly, the object of the invention is to provide novel compounds of rapamycin which are useful as an anti-proliferative agents possessing the general structure of rapamycin wherein, the hydroxyl group in the 42-position has been modified to corresponding 42-O-(heteroalkoxyalkyl) rapamycin compounds and methods for preparing the same.

SUMMARY OF THE INVENTION

In accordance with the above objective, the invention provides novel compounds of rapamycin wherein, the hydroxyl group in the 42-position has been modified to corresponding 42-O-(heteroalkoxyalkyl) rapamycin compounds and methods for preparing the same.

According to one aspect, the invention provides novel 42-O-(heteroalkoxyalkyl) rapamycin compounds of formula 1.

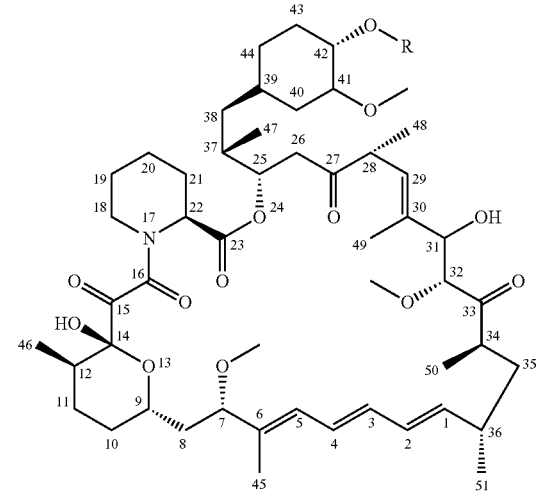

Wherein, R denotes 3, 4 and 5 membered 3-hydroxy heteroalkoxyalkyl compounds Tetrahydrofuran-3-ol, Oxetan-3-ol, Tetrahydropyran-3-ol, Tetrahydro-4-methyl furan-3-ol, Tetrahydro-2,5,5-trimethyl furan-3-ol, Tetrahydro-2,5-diethyl-2-methyl furan-3-ol, Tetrahydro-6-methoxy-2-methyl 2H-Pyran-3-ol and Tetrahydro-2,2-dimethyl-6-phenyl 2H-Pyran-3-ol.

Accordingly, in one preferred embodiment, R is tetrahydrofuran-3-ol to arrive at 42-O-(tetrahydrofuran-3-yl) rapamycin compound, designated herein as Merilimus-1.

In another preferred embodiment, R is oxetan-3-ol to arrive at 42-O-(oxetan-3-yl) rapamycin compound, designated herein as Merilimus-2.

In yet another preferred embodiment, R is tetrahydropyran-3-ol to arrive at 42-O-(tetrahydropyran-3-yl) rapamycin compound, designated herein as Merilimus-3.

In another embodiment, R is 3-Furanol, tetrahydro-4-methyl- to arrive at 42-O-(4-methyl, tetrahydrofuran-3-yl) rapamycin compound.

In yet another embodiment, R is 3-Furanol, tetrahydro-2,5,5-trimethyl- to arrive 42-O-(2,5,5-trimethyl, tetrahydrofuran-3-yl) rapamycin compound.

In another embodiment, R is 3-Furanol, Tetrahydro-2,5-Diethyl-2-Methyl- to arrive at 42-O-(2,5-diethyl-2-methyl, tetrahydrofuran-3-yl) rapamycin compound.

In yet another embodiment, R is 2H-Pyran-3-ol, tetrahydro-6-methoxy-2-methyl- to arrive at 42-O-(2H-Pyran-3-yl, tetrahydro-6-methoxy-2-methyl) rapamycin compound.

In yet another embodiment, R is 2H-Pyran-3-ol, tetrahydro-2, 2-dimethyl-6-phenyl- to arrive at 42-O-(2H-Pyran-3-yl, tetrahydro-2,2-dimethyl-6-phenyl) rapamycin compound.

According to another aspect, the present invention provides a method for making 42-O-(heteroalkoxyalkyl) rapamycin compounds by reacting rapamycin with triflic (trifluoromethanesulfonic) anhydride to prepare triflate intermediate which further on reaction with 3-hydroxy heteroalkoxyalkyl compound yields desired compounds. The details of the synthesis are exemplified below.

Accordingly, the method for making 42-O-(heteroalkoxyalkyl) rapamycin compounds represented by the general formula (1), comprises reaction of rapamycin with triflic anhydride in presence of an organic base and halogenated organic solvent to prepare triflate intermediate which further on reaction with 4, 5 or 6-membered 3-hydroxy heteroalkoxyalkyl compound in presence of trialkyl amine and inert organic solvent yields 42-O-(heteroalkoxyalkyl) rapamycin compounds.

The organic base according to the invention may be selected from pyridine or its derivatives. The pyridine derivative is preferably 2,6 dimethyl pyridine, which is used in amount of 3 to 15 mol per mol of rapamycin.

The triflic anhydride is used in an amount of 1 to 10 mol per mol of the 42-O-(heteroalkoxyalkyl) rapamycin compounds.

The inert organic solvent is selected from halogenated organic solvent, which is used in an amount of 10 to 30 parts by weight for 1 part by weight of rapamycin.

The halogenated organic solvent is selected from the group consisting of methylene chloride, ethylene dichloride, chlorobenzene or chloroform.

The trialkyl amine is selected from triethyl amine, N,N-Diisopropylethylamine or N,N-Di-n-butylethylamine and is used in the reaction in an amount of 5 to 20 mol per mol of rapamycin.

The 3-hydroxy heteroalkoxyalkyl compound for the purpose of the invention is selected from Oxetan-3-ol, Tetrahydrofuran-3-ol, Tetrahydro-4-methyl furan-3-ol, Tetrahydro-2,5,5-trimethyl furan-3-ol, Tetrahydro-2, 5-diethyl-2-methyl furan-3-ol, Tetrahydropyran-3-ol, Tetrahydro-6-methoxy-2-methyl 2H-Pyran-3-ol and Tetrahydro-2,2-dimethyl-6-phenyl 2H-Pyran-3-ol.

The 3-hydroxy heteroalkoxyalkyl compound is used in the reaction in an amount of 1 to 7 mol per mol of rapamycin.

The crude 42-O-(heteroalkoxyalkyl) rapamycin compounds obtained according to the method of invention is purified by two stage purification by preparative HPLC using two different columns.

The first stage of purification is done by preparative HPLC in an amount of 5 to 25 parts by weight for 1 part by weight of the crude 42-O-(heteroalkoxyalkyl) rapamycin compound followed by passing through second stage of column purification to get 42-O-(heteroalkoxyalkyl) rapamycin compound with purity of at least about 95% area by HPLC, more preferably at least about 98% area by HPLC.

The 42-O-(heteroalkoxyalkyl) rapamycin compound obtained according to the process of present invention is further stabilized by the addition of an anti-oxidant for enhancing a storage stability of 42-O-(heteroalkoxyalkyl) rapamycin compounds.

The preferable anti-oxidant is selected from butylated hydroxy toluene (BHT), DL-α-tocopherol, propyl gallate, ascorbyl palmitate, 3-tert-butyl-4-hydroxyanisole, 2-tert-butyl-4-hydroxyanisole, and fumaric acid.

The anti-oxidant as used is 0.1% to 1.0% (w/w) based on 100% (w/w) of said 42-O-(heteroalkoxyalkyl) rapamycin compound.

In a further aspect, 42-O-(heteroalkoxyalkyl) rapamycin compounds prepared according to the invention are tested for their biological activities like, haemocompatibility, haemolysis and cytotoxicity. The potency of 42-O-(heteroalkoxyalkyl) rapamycin compounds also assessed for anti-proliferation effect in comparison with rapamycin.

In yet another aspect, the invention provides pharmaceutical compositions comprising 42-O-(heteroalkoxyalkyl) rapamycin compounds of formula 1 in association with one or more pharmaceutical carrier/excipients. The pharmaceutical compositions incorporating 42-O-(heteroalkoxyalkyl) rapamycin compounds can be prepared into various formulations for achieving desired therapeutic/clinical effect. Methods of making such formulations are well known in the art, where the active ingredient is mixed with suitable pharmaceutical excipient/carrier to yield desired formulation suitable for oral, injectable, parenteral, local administration or coating on implantable medical devices.

In yet another aspect, the invention provides method of preventing or treating hyperproliferative vascular disease selected from the group consisting of restenosis and vascular occlusion in a mammal by administering compound of formula 1 in association with one or more pharmaceutical carriers to said subject orally, parenterally, intravascularly, or via an implantable medical device impregnated with the compound of Formula 1 in association with one or more pharmaceutical carriers.

In yet another aspect, the invention provides method of preventing or treating arterial restenosis in a mammal by implanting a medical device coated with an effective amount of 42-O-(heteroalkoxyalkyl) rapamycin compounds of formula 1 in association with one or more pharmaceutical carriers.

In a further aspect, the invention provides use of 42-O-(heteroalkoxyalkyl) rapamycin compounds of formula 1 for the preparation of medicament for the treatment of hyperproliferative vascular disease.

In a further aspect, the invention provides use of 42-O-(heteroalkoxyalkyl) rapamycin compounds of formula 1 for coating on implantable medical device for the treatment of arterial restenosis.

DETAIL DESCRIPTION OF THE INVENTION

Figure 1A:
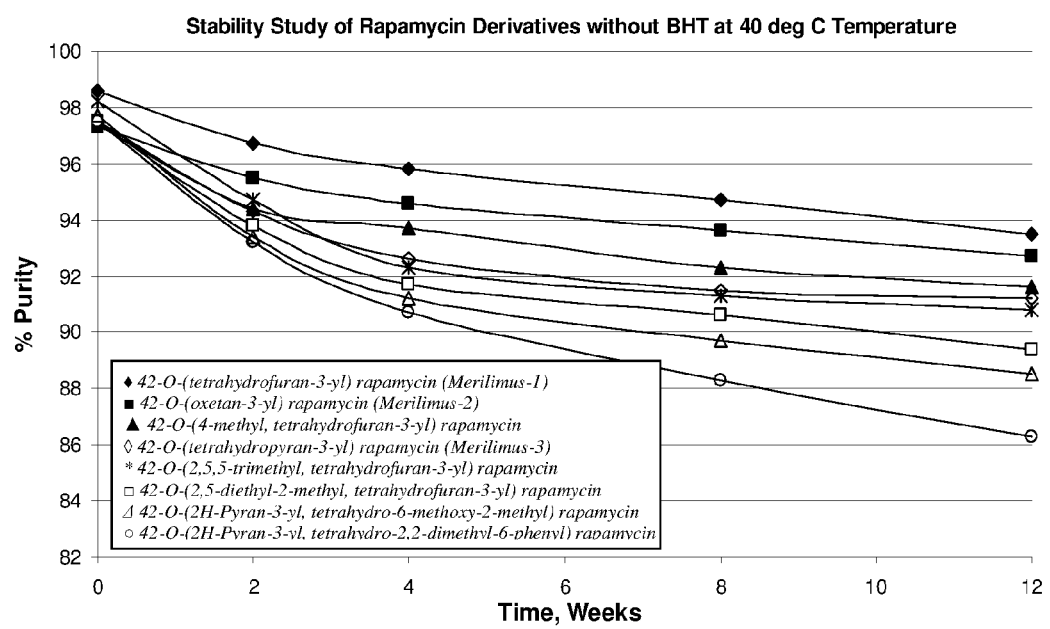
FIG. 1A shows thermal effect on stability of various 42-O-(heteroalkoxyalkyl) rapamycin compounds without BHT at 40° C. Temperature up to 12 weeks period.
Figure 1B:
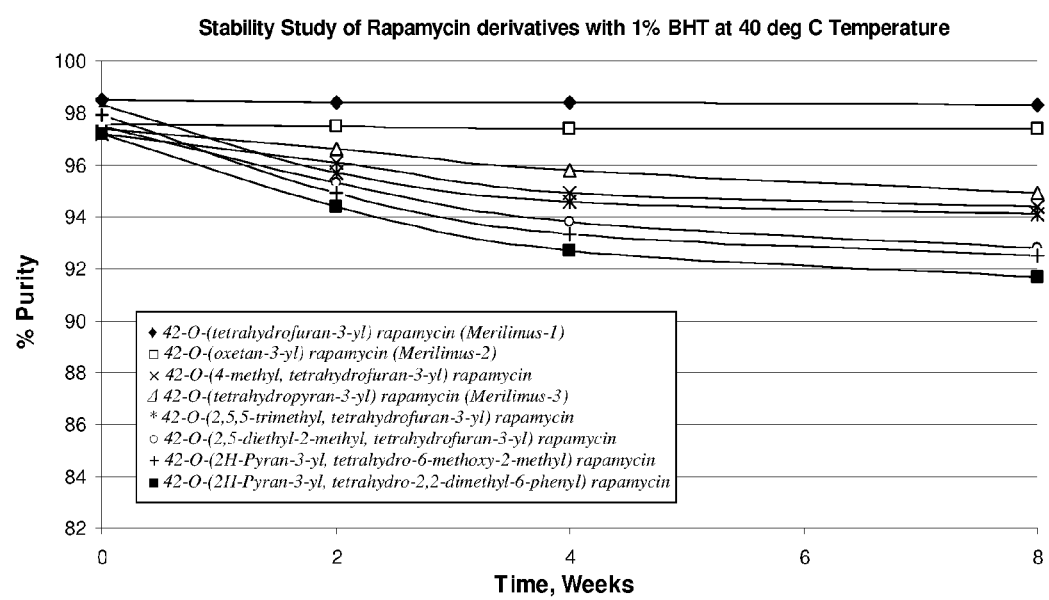
FIG. 1B shows effect of anti-oxidant (1% BHT) on stability of various 42-O-(heteroalkoxyalkyl) rapamycin compounds at 40° C. temperature up to 8 weeks period.

The invention will now be described in detail in connection with certain preferred and optional embodiments, so that various aspects thereof may be more fully understood and appreciated.

Accordingly, the present invention discloses 42-O-(heteroalkoxyalkyl) rapamycin compounds of general structural formula (1) and chemical method for making purified 42-O-(heteroalkoxyalkyl) rapamycin compounds.

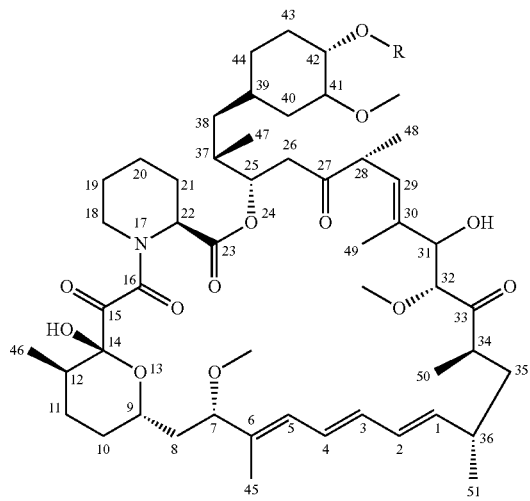

Wherein, R denotes 3, 4 and 5 membered 3-hydroxy heteroalkoxyalkyl compounds selected from Tetrahydrofuran-3-ol, Oxetan-3-ol, Tetrahydropyran-3-ol,Tetrahydro-4-methyl furan-3-ol, Tetrahydro-2,5,5-trimethyl furan-3-ol, Tetrahydro-2,5-diethyl-2-methyl furan-3-ol, Tetrahydro-6-methoxy-2-methyl 2H-Pyran-3-ol and Tetrahydro-2,2-dimethyl-6-phenyl 2H-Pyran-3-ol.

Accordingly, the present invention encompasses the following compounds of 42-O-(heteroalkoxyalkyl) rapamycin of formulas (8) to (15).

1. Tetrahydrofuran-3-ol compound

Formula (8)

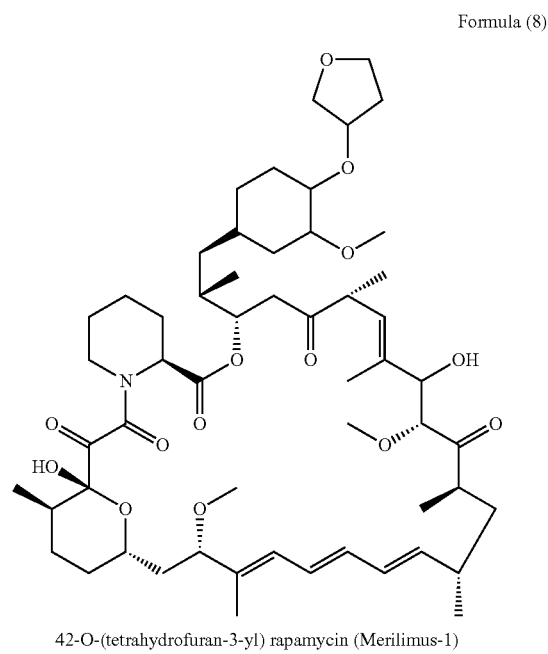

42-O-(tetrahydrofuran-3-yl) rapamycin (Merilimus-1)

2. 4-methyl, tetrahydrofuran-3-ol compound

Formula (9)

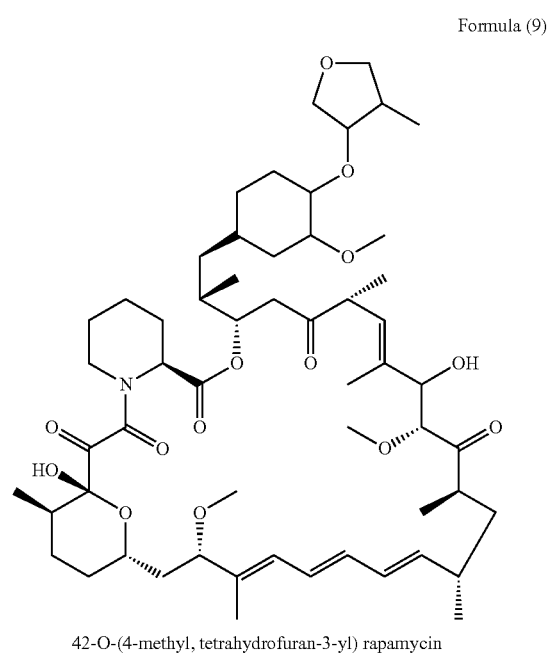

42-O-(4-methyl, tetrahydrofuran-3-yl) rapamycin 3. 2,5,5-trimethyl, tetrahydrofuran-3-ol compound
Formula (10)
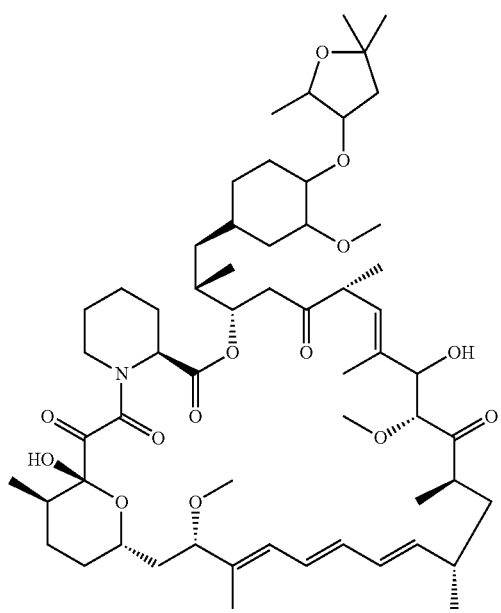
42-O-(2,5,5-trimethyl, tetrahydrofuran-3-yl) rapamycin
4. 2,5-diethyl-2-methyl, tetrahydrofuran-3-ol-compound
Formula (11)
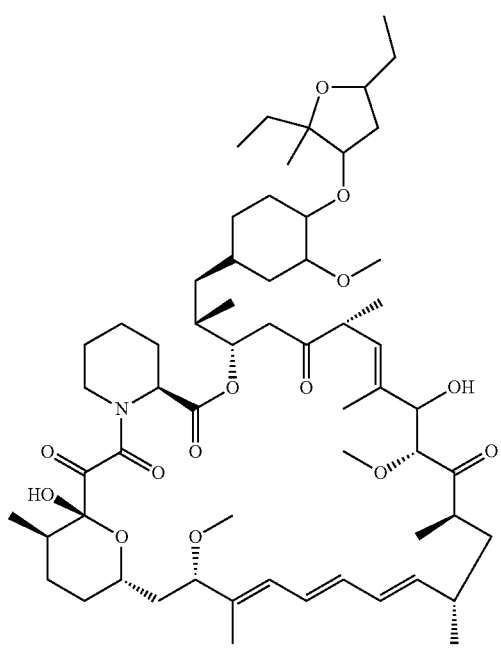
42-O-(2,5-diethyl-2-methyl, tetrahydrofuran-3-yl) rapamycin
5. Oxetan-3-ol compound
Formula (12)
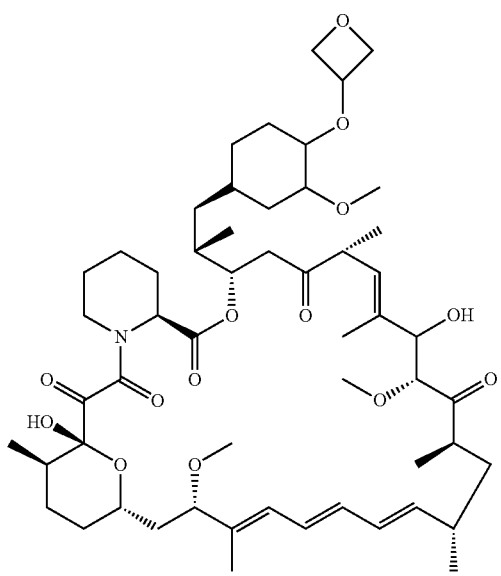
42-O-(oxetan-3-yl) rapamycin (Merilimus-2)
6. Tetrahydropyran-3-ol compound
Formula (13)
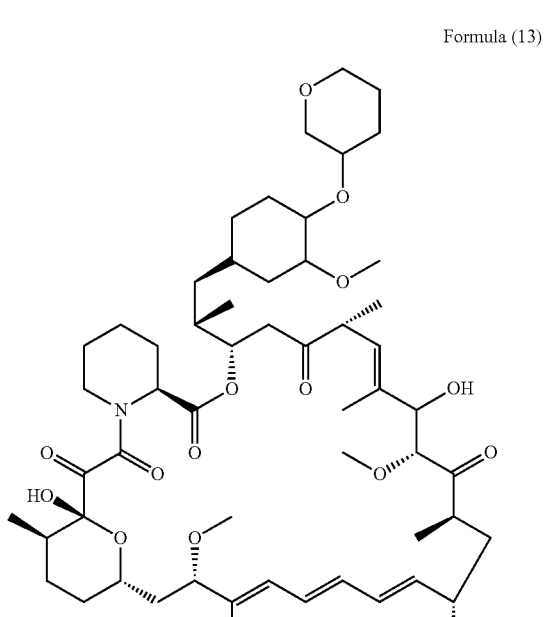
42-O-(tetrahydropyran-3-yl) rapamycin (Merilimus-3)

-continued 7. 42-O-(2H-Pyran-3-ol, tetrahydro-6-methoxy-2-methyl) compound

Formula (14)

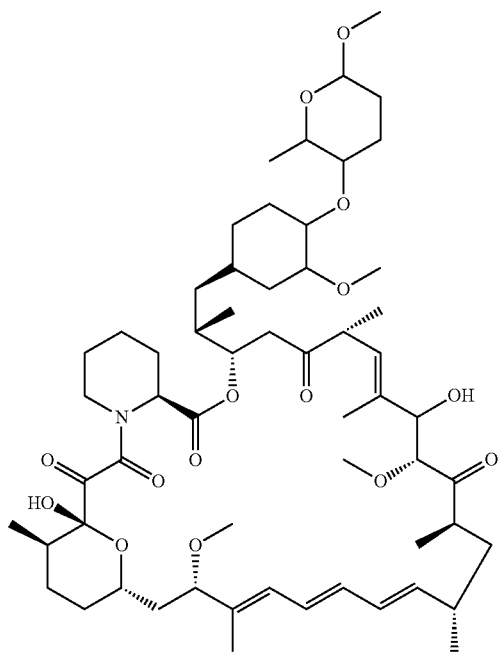

42-O-(2H-Pyran-3-yl, tetrahydro-6-methoxy-2-methyl) rapamycin 8. 2H-Pyran-3-ol, tetrahydro-2,2-dimethyl-6-phenyl- compound Formula (15)

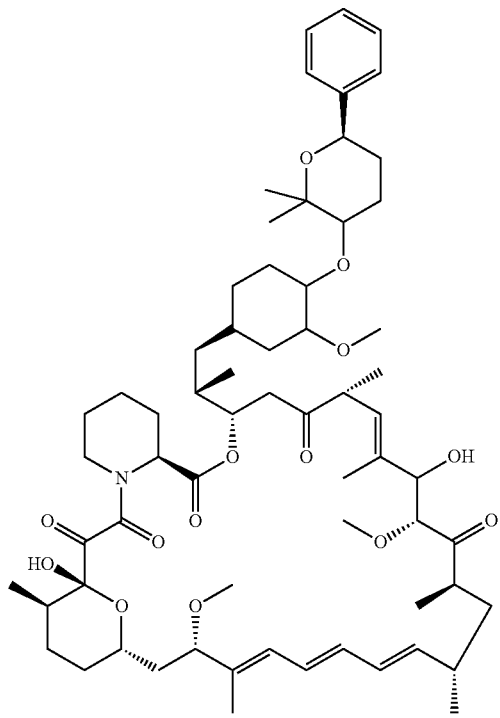

42-O-(2H-Pyran-3-yl, tetrahydro-2,2-dimethyl-6-phenyl) rapamycin

In another embodiment, the invention describes the processes for 42-O-(tetrahydrofuran-3-yl) rapamycin compounds.

According to the process of the present invention, the starting reactant rapamycin of formula (2) is reacted with trifluoromethanesulfonic anhydride of formula (3) using an organic base of pyridine derivative of formula (4) as catalyst and in the presence of an halogenated organic solvent to obtain triflate intermediate of formula (5). This intermediate is further subjected to displacement reaction with 4, 5 or 6 membered 3-hydroxy heteroalkoxyalkyl compound of formula (6a), (6b) or (6c) in presence of a trialkyl amine of formula (7) and halogenated organic solvent to obtain 42-O-(heteroalkoxyalkyl) rapamycin compounds of general formula (1), which are separated and passed through two stages of column purification process to get purified compounds (8-15). Purified 42-O-(heteroalkoxyalkyl) rapamycin compounds (8-15) thus obtained are observed to be somewhat unstable at room temperature and therefore the same are stabilized by addition of phenolic anti-oxidants in acetone, such as BHT (2,6-di-t-butyl-4-methylphenol, Butylated hydroxy toluene). This homogenous mixture is then isolated and dried by lyophilisation to get final solid derivative.

The formulae, definitions and detailed description for the related reactants, base, solvent and products are further described as follows:

Rapamycin

Rapamycin as used herein is a starting reactant having structure presented by the following formula:

Formula (2)

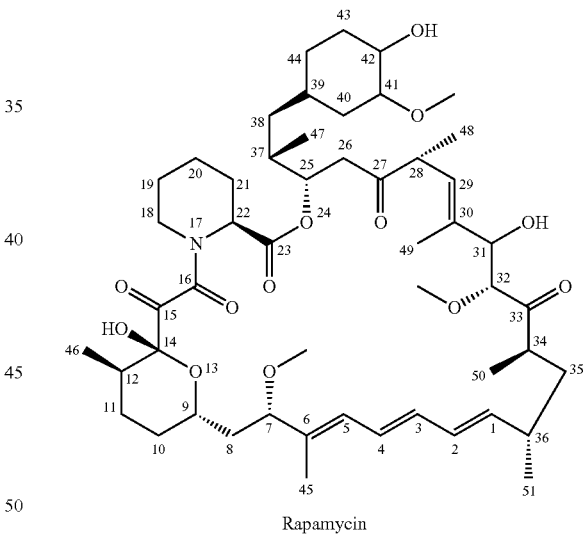

Rapamycin

Alkyl Triflate

A method according to present invention, wherein said alkyl triflate is trifluoromethanesulfonic anhydride.

Formula (3)

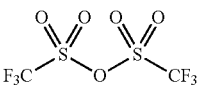

Trifluoromethanesulfonic (Triflic) anhydride

This renders high stability, high activity and sound tractability to be beneficial for the reaction of the present invention. It can be stored at room temperature.

Organic Base

The organic base is used as catalyst and may be selected from pyridine derivatives of formula (4).

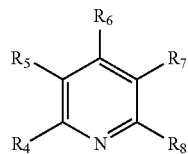

Formula (4)

Wherein $R_4$, $R_5$, $R_6$, $R_7$ and $R_8$ are each individually selected from hydrogen and $C_1$–$C_{10}$ alkyl substitutions.

A method according to present invention, wherein said pyridine derivative is 2,6-dimethyl pyridine.

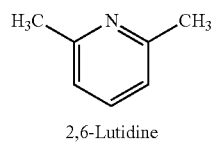

2,6-Lutidine

Organic Solvent

The organic solvent may be selected from alkyl halide and other suitable inert halogenated organic solvents selected from ethylene chloride, methylene chloride, chlorobenzene or chloroform.

Triflate Intermediate

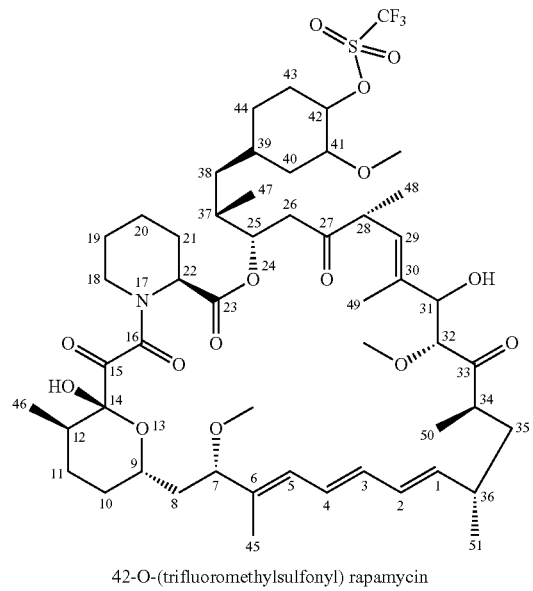

Formula (5)

42-O-(trifluoromethylsulfonyl) rapamycin

Wherein trifluoromethane sulfonic anhydride is selected for the preparation of the triflate group, which is then reacted with a molecule of 3-hydroxy heteroalkoxyalkyl compounds of formula (6a), (6b) and (6c) to obtain 42-O-(heteroalkoxyalkyl) rapamycin compounds of formula (1), wherein R is selected from the 4, 5 and 6 membered 3-hydroxy heteroalkoxyalkyl compounds of formula (6a), (6b) and (6c) as shown below:

4 Membered Ring

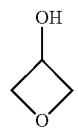

Formula (6a)

Oxetan-3-ol

5 Membered Ring

Formula (6b)

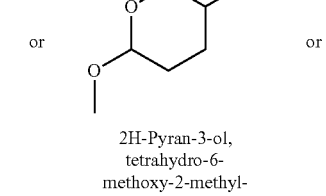

Tetrahydrofuran-3-ol  or  3-Furanol, tetrahydro-4-methyl-  or  3-Furanol, tetrahydro-2,5,5-trimethyl- 3-Furanol, Tetrahydro-2,5-Diethyl-2-Methyl- 6 Membered Ring Formula (6c)

Tetrahydropyran-3-ol  or  2H-Pyran-3-ol, tetrahydro-6-methoxy-2-methyl-  or

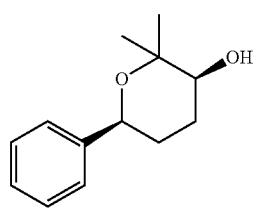

2H-Pyran-3-ol, tetrahydro-2,2-dimethyl-6-phenyl-

Trialkyl Amine

Formula (7)

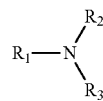

Wherein $R_1$, $R_2$ and $R_3$ are each selected from $C_1$~$C_{10}$ alkyl substituents respectively, A method according to present invention, said trialkyl amine is N,N-Di-isopropylethylamine or N,N-Di-n-butylethylamine.

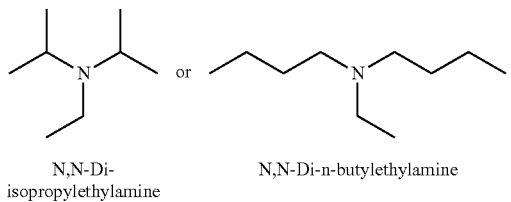

N,N-Di-isopropylethylamine    N,N-Di-n-butylethylamine

The compounds of 42-O-(heteroalkoxyalkyl) rapamycin encompass formulas (8) to (15).

Formula (8)

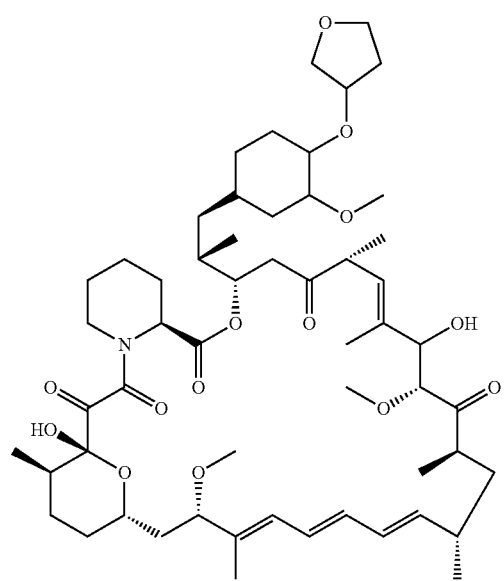

Tetrahydrofuran-3-ol compound
42-O-(tetrahydrofuran-3-yl) rapamycin (Merilimus-1)

Referring to the above compound (8), wherein the hydroxyl group at carbon number 42 in the rapamycin is modified with a moiety of tetrahydrofuran-3-ol compound.

Formula (9)

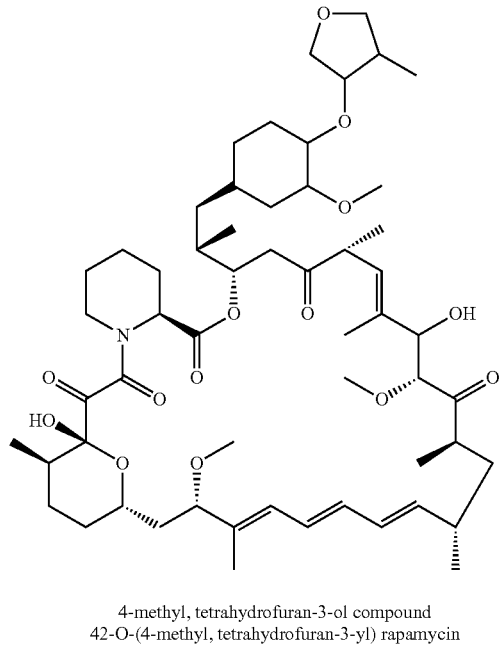

4-methyl, tetrahydrofuran-3-ol compound
42-O-(4-methyl, tetrahydrofuran-3-yl) rapamycin Referring to the above compound (9), wherein the hydroxyl group at carbon number 42 in the rapamycin is modified with a moiety of 4-methyl, tetrahydrofuran-3-ol compound.

Formula (10)

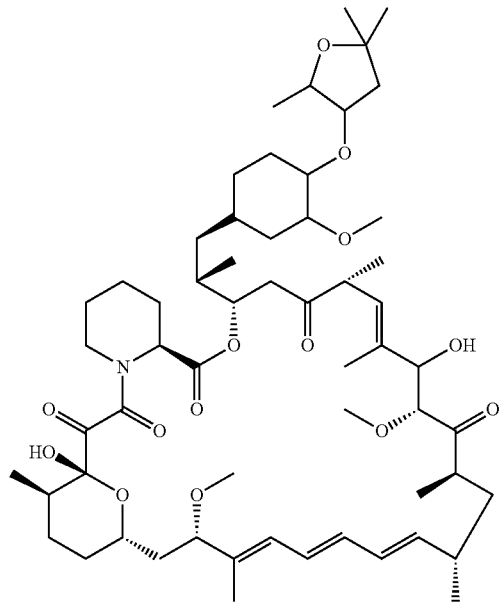

2,5,5-trimethyl, tetrahydrofuran-3-ol compound
42-O-(2,5,5-trimethyl, tetrahydrofuran-3-yl) rapamycin Referring to the above compound (10), wherein the hydroxyl group at carbon number 42 in the rapamycin is modified with a moiety of 2,5,5-trimethyl, tetrahydrofuran-3-ol compound.

Formula (11)

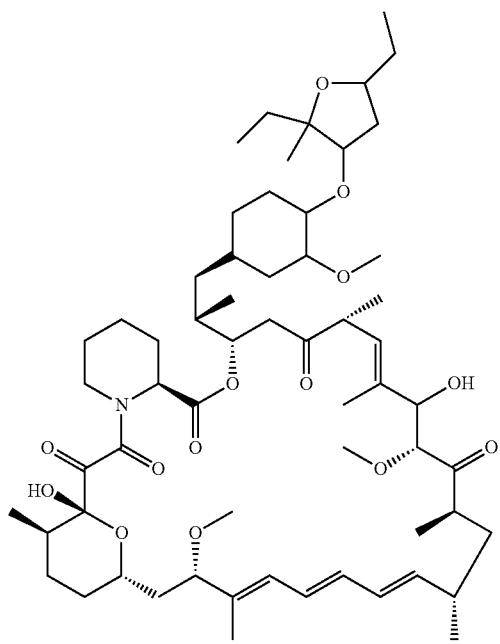

2,5-diethyl-2-methyl, tetrahydrofuran-3-ol compound
42-O-(2,5-diethyl-2-methyl, tetrahydrofuran-3-yl) rapamycin Referring to the above compound (11), wherein the hydroxyl group at carbon number 42 in the rapamycin compound is modified with a moiety of 2,5-diethyl-2-methyl, tetrahydrofuran-3-ol compound.

Formula (12)

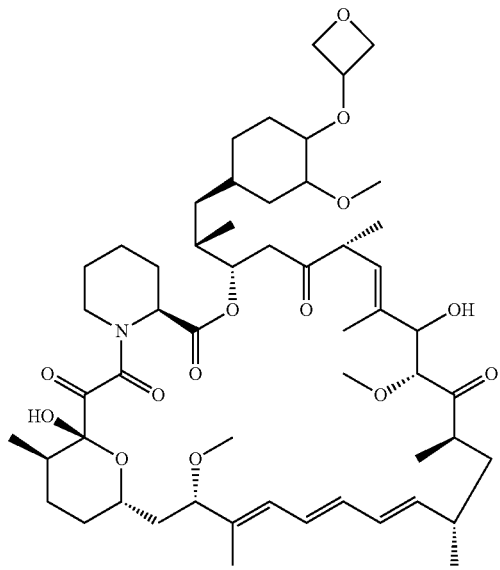

Oxetan-3-ol compound
42-O-(oxetan-3-yl) rapamycin (Merilimus-2)

Referring to the above compound (12), wherein the hydroxyl group at carbon number 42 in the rapamycin compound is modified with a moiety of Oxetan-3-ol compound.

Formula (13)

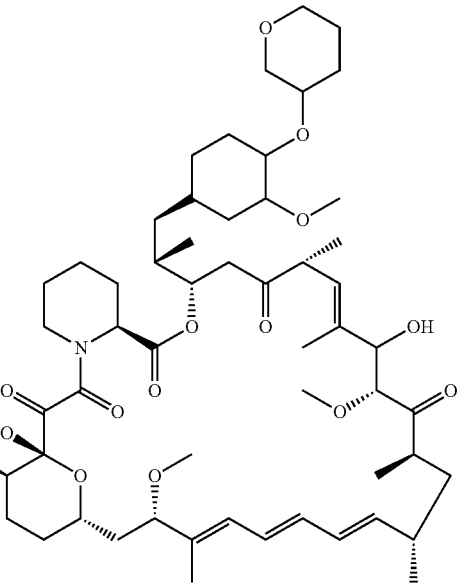

Tetrahydropyran-3-ol compound
42-O-(tetrahydropyran-3-yl) rapamycin (Merilimus-3)

Referring to the above compound (13), wherein the hydroxyl group at carbon number 42 in the rapamycin compound is modified with a moiety of tetrahydropyran-3-ol compound.

Formula (14)

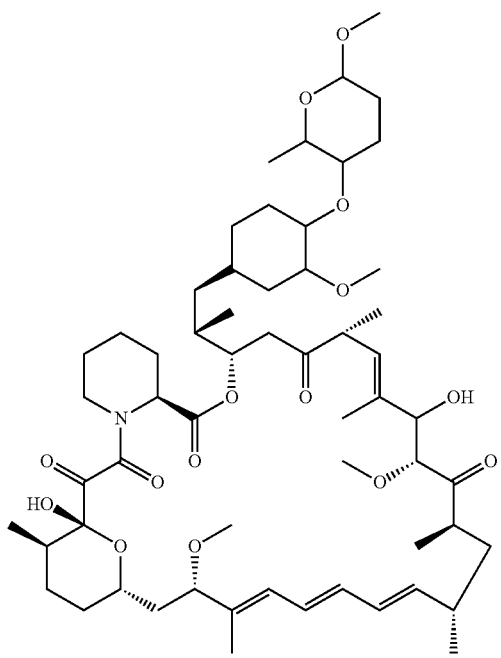

42-O-(2H-Pyran-3-ol, tetrahydro-6-methoxy-2-methyl) compound
42-O-(2H-Pyran-3-yl, tetrahydro-6-methoxy-2-methyl) rapamycin Referring to the above compound (14), wherein the hydroxyl group at carbon number 42 in the rapamycin compound is modified with a moiety of 2H-Pyran-3-ol, tetrahydro-6-methoxy-2-methyl compound.

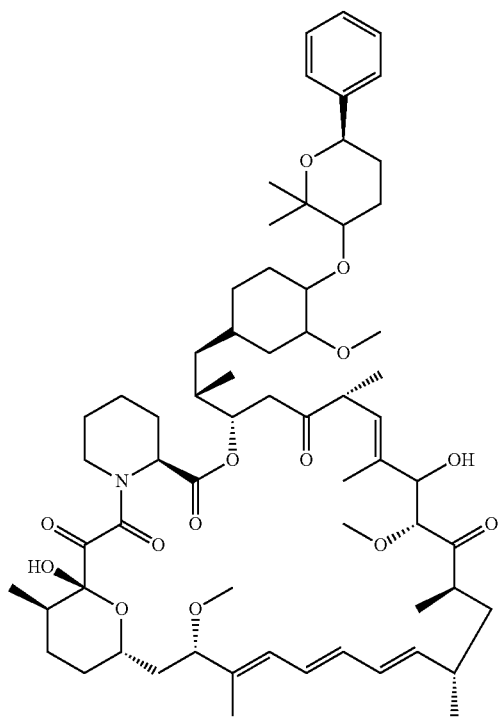

Formula (15)

2H-Pyran-3-ol, tetrahydro-2,2-dimethyl-6-phenyl-compound
42-O-(2H-Pyran-3-yl, tetrahydro-2,2-dimethyl-6-phenyl) rapamycin Referring to the above compound (15), wherein the hydroxyl group at carbon number 42 in the rapamycin compound is modified with a moiety of 2H-Pyran-3-ol, tetrahydro-2,2-dimethyl-6-phenyl compound.

The rapamycin, 42-O-(heteroalkoxyalkyl) compounds of the invention are prepared in two reaction steps. In step-1, the 42-hydroxyl group of rapamycin is activated with alkyl triflate in presence of an organic base and inert organic solvent to form triflate intermediate. In the synthesis of triflate intermediate for 42-O-(heteroalkoxyalkyl) rapamycin compounds, the organic solvent is not specifically restricted to halogenated solvent as long as it dissolves the starting materials and the reaction products.

In the synthesis of triflate intermediate for 42-O-(heteroalkoxyalkyl) rapamycin compound, the organic solvent should be used in an amount not less than 15 parts by weight; preferably 15 to 20 parts by weight, for 1 part by weight of rapamycin.

Accordingly, rapamycin, 42-O-(trifluoromethylsulfonyl) having a leaving group (triflate intermediate) is readily prepared by reaction of dry rapamycin with corresponding trifluoromethylsufonic anhydride, in the presence of inert methylene chloride and 2,6-lutidine as catalyst under cooled temperature conditions and inert nitrogen gas environment. In the synthesis of triflate intermediate for 42-O-(heteroalkoxyalkyl) rapamycin compounds by the process according to the present invention, the trifluoromethanesulfonic (triflic) anhydride should be used in an amount not less than 3 mol, preferably 3 to 7 mol, per mol of rapamycin.

In the synthesis of triflate intermediate for 42-O-(heteroalkoxyalkyl) rapamycin compounds by the process according to the present invention, the 2,6-Lutidine should be used in an amount not less than 6 mol, preferably 6 to 10 mol, per mol of rapamycin. The 2,6-lutidine is added in the reaction to prevent an increase in the acidity of the reaction mixture, as during the reaction, the activating agent trifluoromethylsufonic anhydride forms trifluoromethanesulfonic acid. Thus 2,6-lutidine acts as an acid scavenger in order to move the reaction in forward direction. In the synthesis of triflate intermediate, the reaction temperature is −10 to −60° C., preferably being −20 to −40° C. temperature.

In the synthesis of triflate intermediate for 42-O-(heteroalkoxyalkyl) rapamycin compounds, after addition of trifluoromethanesulfonic (triflic) anhydride; the reaction mixture is allowed to warm to −20 to 10° C. temperature, preferably at −20 to 0° C. temperature.

In the synthesis of triflate intermediate for 42-O-(heteroalkoxyalkyl) rapamycin compounds, the reaction mixture is stirred to 10 to 80 minutes, preferably being 20 to 40 minutes to get pale yellow viscous mass.

In step-2, 42-O-(heteroalkoxyalkyl) rapamycin compound is prepared by displacement of the leaving group with the 3-hydroxy heteroalkoxyalkyl compound in presence of suitable trialkyl amine catalyst, selected from N,N-Di-n-butylethylamine or N,N Di-isopropylethylamine.

In the synthesis of 42-O-(heteroalkoxyalkyl) rapamycin compounds from triflate intermediate, N,N-di-isopropylethylamine or N,N-Di-n-butylethylamine should be used in an amount not less than 10 mol, preferably 10 to 15 mol, per mol of rapamycin.

In the synthesis of 42-O-(heteroalkoxyalkyl) rapamycin compounds from triflate intermediate, after displacement with 3-hydroxy heteroalkoxyalkyl compound; the reaction mixture is allowed to warm to −20 to 10° C. temperature, preferably at −10 to 10° C. temperature.

In the synthesis of 42-O-(heteroalkoxyalkyl) rapamycin compounds from triflate intermediate, after displacement with 3-hydroxy heteroalkoxyalkyl compound; the reaction mixture is stirred to 12 to 96 hours, preferably being 36 to 60 hours at 5 to 35° C. temperature, preferably at 10 to 25° C. temperature.

The 3-hydroxy heteroalkoxyalkyl compounds are selected for the purpose of the present invention are among the products readily available commercially such as Oxetan-3-ol, Tetrahydrofuran-3-ol, Tetrahydro-4-methyl furan-3-ol, Tetrahydro-2,5,5-trimethyl furan-3-ol, Tetrahydro-2, 5-diethyl-2-methyl furan-3-ol, Tetrahydropyran-3-ol, Tetrahydro-6-methoxy-2-methyl 2H-Pyran-3-ol, Tetrahydro-2,2-dimethyl-6-phenyl 2H-Pyran-3-ol, etc.

The crude 42-O-(heteroalkoxyalkyl) rapamycin compound obtained according to the reactions as explained above is concentrated by evaporation under reduced pressure to provide a pale yellow viscous mass, which is purified and isolated in a conventional manner like extraction, precipitation, fractional crystallization, recrystallization, chromatography, and the like.

In all the embodiments, the desired 42-O-(heteroalkoxyalkyl) rapamycin compounds are easily separated from the side products preferably by two purification stages, such as preparative HPLC and combiflash column chromatography methods.

Since the purified 42-O-(heteroalkoxyalkyl) rapamycin compound is a polyene macrolide, which has a tendency to oxidize and decompose during the storage or handling. Therefore, to enhance the stability, a proper antioxidant in acetone is mixed with the concentrated 42-O-(heteroalkoxyalkyl) rapamycin compound before proceeding to isolation and drying steps.

The suitable antioxidants may be selected from; Butylated hydroxytoluene (BHT), DL-α-tocopherol, propyl gallate, ascorbyl palmitate, 3-tert-butyl-4-hydroxyanisole, 2-tert-butyl-4-hydroxyanisole, and fumaric acid.

The 3,5-di-tert-4-butyl hydroxy toluene (BHT) is the most preferable antioxidant adapted for use in the present invention.

The homogeneous reaction mixture obtained according to process as explained above is finally isolated and dried to obtain the 42-O-(heteroalkoxyalkyl) rapamycin compound of the present invention with an isolated good yield.

The purified 42-O-(heteroalkoxyalkyl) rapamycin compound is a white powder and it can be easily used for coating of medical device, handling, storage and stability.

The purified 42-O-(heteroalkoxyalkyl) rapamycin compounds thus obtained is analysed and identified by spectral studies like Nuclear Magnetic Resonance (NMR), Mass Spectra (MS) and High Performance Liquid Chromatography (HPLC).

In yet another embodiment, the invention provides pharmaceutical compositions comprising 42-O-(heteroalkoxyalkyl) rapamycin compounds of formula 1 in association with one or more pharmaceutical carrier/excipients. The pharmaceutical compositions incorporating a 42-O-(heteroalkoxyalkyl) rapamycin compounds can be prepared into various formulations for achieving desired therapeutic/clinical effect. Methods of making such formulations are well known in the art, where the active ingredient is mixed with suitable pharmaceutical excipient/carrier/substrate to yield desired formulation suitable for oral, injectable, parenteral, local administration or coating on implantable medical devices. The pharmaceutical excipient/carrier used includes diluents, lubricants, binders, emulsifiers, disintegrators, effervescent mixtures, adsorbents, colors, flavors, and sweeteners etc. The diluents are selected from lactose, dextrose, sucrose, mannitol, sorbitol, cellulose, glycerol etc. The lubricants are selected from silicic acid, talc, stearic acid, or salts thereof such as calcium or magnesium stearate, polyethylene glycol, etc. The binders are selected from magnesium aluminum silicate, starches such as corn, wheat or rice starch, gelatin, methylcellulose, carboxymethyl cellulose, polyvinyl pyrrolidone etc. The disintegrators are selected from starches, agar, alginic acid, or its sodium salt etc.

Examples of typical formulations for coating on medical devices like coronary or other vascular stents are described herein below. It is understood that other compositions of formulations are also possible and one should not assume that these are the only possible formulations of the compounds of formula 1.

The compositions described below can be used for vascular treatment specifically to prevent arterial restenosis. Formulation containing nano size particles can also be used for administration by parenteral or oral route or through direct delivery to the site of disease by implanting a medical device, such as a stent or balloon catheter; where the drug is coated on either the stent or on the balloon of the catheter.

The substrate/carrier/excipient particles serve to bind the 42-O-(heteroalkoxyalkyl) rapamycin compounds and to control the release rate of drug from the formulation. The formulation can optionally be converted into nanoparticles. Suitable substrates are lipid/s or biodegradable/non-degradable polymer/s and nano particles thereof. These substrates are safe and have history of usage in the systemic circulation.

Substrates suitable for formulation are numerous and varied; the general selection criterion being a substrate capable of carrying a 42-O-(heteroalkoxyalkyl) rapamycin compounds.

The biodegradable polymer substrates may include, but are not limited to poly lactide, poly glycolide, poly (lactide-co-glycolide), poly(glycolic acid-co-trimethylene carbonate), poly caprolactone, polyvinyl alcohol (PVA), polyvinyl pyrrolidone (PVP), ethylene vinyl alcohol, poly(hydroxyvalerate), poly(hydroxybutyrate); poly(hydroxybutyrate-co-valerate), polydioxanone; polyorthoester; polyanhydride and mixtures thereof. The non-degradable polymer substrates may include, but are not limited to polyurethanes; silicones; polyesters; polyolefins; polyisobutylene and ethylene-alpha-olefin copolymers; acrylic polymers and copolymers; vinyl halide polymers and copolymers, such as polyvinyl chloride; polyvinyl ethers, such as polyvinyl methyl ether; polyvinylidene halides, such as polyvinylidene fluoride and polyvinylidene chloride; polyacrylonitrile; polyvinyl ketones; polyvinyl aromatics, such as polystyrene; polyvinyl esters, such as polyvinyl acetate; copolymers of vinyl monomers with each other and olefins, such as ethylene-methyl methacrylate copolymers, acrylonitrilestyrene copolymers, cellulose; cellulose acetate; cellulose butyrate; cellulose acetate butyrate; cellophane; cellulose nitrate; cellulose propionate; cellulose ethers; and carboxymethyl cellulose, polyamides, such as Nylon 66 and polycaprolactam and mixtures thereof.

Lipid substrates may include, but are not limited to hydrogenated castor oil, hydrogenated palm oil, hydrogenated soybean oil, hydrogenated cottonseed oil, hydrogenated peanut oil, hydrogenated coconut oil, hydrogenated Turkish red oil, hydrogenated olive oil, hydrogenated isobutene oil and mixtures thereof.

In another embodiment, the invention provides a method of treating hyperproliferative vascular disease selected from the group consisting of restenosis and vascular occlusion in a mammal by administering an antiproliferative effective amount of 42-O-(heteroalkoxyalkyl) rapamycin compounds of formula 1 in association with one or more pharmaceutical carriers to said mammal orally, parenterally, intravascularly, or via an implantable medical device coated with the vascular stent impregnated with 42-O-(heteroalkoxyalkyl) rapamycin compounds of formula 1. The restenosis, and vascular occlusion in a mammal may be caused due to infectious or a metabolic disorder.

In a further embodiment, the invention provides method of preventing or treating restenosis in a mammal by implanting a medical device coated with an effective amount of 42-O-(heteroalkoxyalkyl) rapamycin compounds of formula 1 in association with one or more pharmaceutical carriers.

In a further embodiment, the invention provides use of 42-O-(heteroalkoxyalkyl) rapamycin compounds of formula 1 for the preparation of medicament for the treatment of hyperproliferative vascular disease.

In a further embodiment, the invention provides use of 42-O-(heteroalkoxyalkyl) rapamycin compounds of formula 1 for coating on implantable medical device for the treatment of arterial restenosis.

A biocompatibility study of 42-O-(tetrahydrofuran-3-yl) rapamycin and 42-O-(oxetan-3-yl) rapamycin compounds are tested in-vitro. The testing details for cytotoxicity, haemolysis and haemocompatibility study are described in Example-3 and the results are shown in Table 3a, 3b, $3c_1$ and $3c_2$.

Potency study of 42-O-(tetrahydrofuran-3-yl) rapamycin and 42-O-(oxetan-3-yl) rapamycin compounds are tested in-vitro and compared to the potency of parent molecule, rapamycin. The testing procedure is described in Example-4 and the results are shown in FIGS. 3*a* and 3*b*.

The process of 42-O-(heteroalkoxyalkyl) rapamycin compounds will be better understood in connection with the synthetic method of the present invention.

The following examples, which include preferred embodiments, will serve to illustrate the practice of this invention, it being understood that the particulars shown are by way of example and for purpose of illustrative discussion of preferred embodiments of the invention.

EXAMPLES

Example 1

The process for efficient production of 42-O-(heteroalkoxyalkyl) rapamycin compounds in accordance with the present invention will be described in detail in view of the following examples:

Example 1A

STEP 1: Conversion of 42-O Hydroxy of Rapamycin to a Trifluoromethanesulfonate Leaving Group In a round bottom reaction flask (100 ml, flame dried) equipped with magnetic stirrer, 4.2 grams (4.6 mmol) of dried rapamycin, 2.95 grams (27 mmol) 2, 6-dimethyl pyridine and 42 ml dichloromethane were added. The reaction mixture was degassed and purged the nitrogen gas into the flask and stirred.

The reaction mixture in the flask was then cooled to −30° C. temperature in acetonitrile-dry ice bath, and was slowly dripped therein with 3.96 grams (13.8 mmol) trifluoromethane sulfonic (triflic) anhydride in 10 ml dichloromethane under agitation. After dripping, the reaction solution was allowed to warm to −10° C. temperatures and stirred between −10 to 0° C. temperature for 30 minutes to get triflate intermediate for step-1. The reaction mixture became a pale yellow viscous mass. HPLC analysis indicated no residual rapamycin remained, which indicated completion of the reaction.

REACTION SCHEME-A

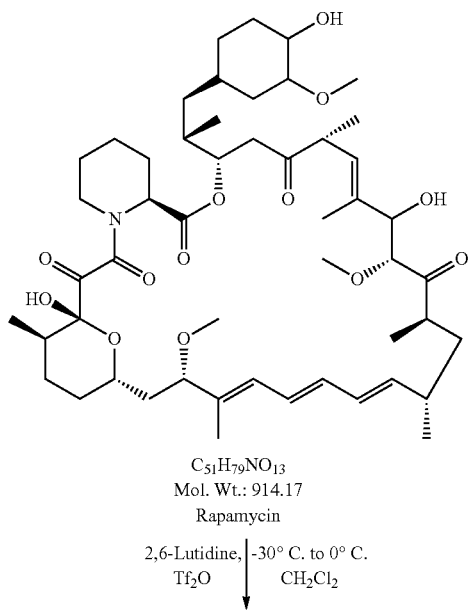

$C_{51}H_{79}NO_{13}$
Mol. Wt.: 914.17
Rapamycin 2,6-Lutidine, −30° C. to 0° C.
Tf$_2$O      CH$_2$Cl$_2$ -continued

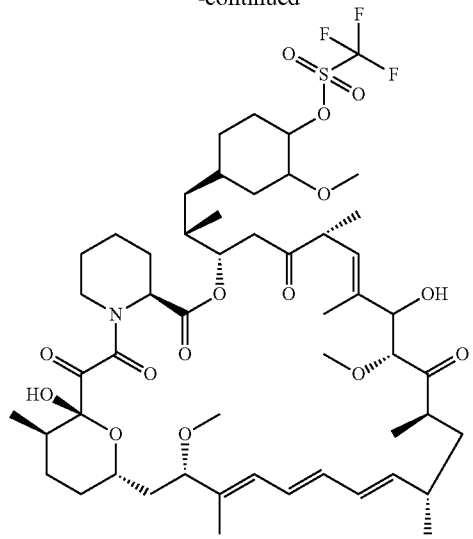

$C_{52}H_{78}F_3NO_{15}S$
Mol. Wt.: 1046.23
Triflate Intermediate

Example 1B

STEP 2: Displacement of the Leaving Group with 5 Membered 3-Hydroxyheteroalkoxyalkyl Compounds to Synthesize 42-O-(Heteroalkoxyalkyl) Rapamycin Compound Preparation of 42-O-(tetrahydrofuran-3-yl), rapamycin (Merilimus 1)

A reaction flask, containing triflate intermediate of step-1 was again cooled to −30° C. temperature and 5.94 grams (46 mmol) of N, N-Diisopropylethylamine (DIPEA) followed by 1.2 grams (13.8 mmol) of tetrahydrofuran-3-ol compound in methylene chloride were added. The reaction mixture was stirred at 0° C. temperature for 12 hours. The reaction mixture was then allowed to warm to 25° C. temperature and continuously stirred for 48 hours.

The reaction mixture was further concentrated by evaporation under reduced pressure to provide a pale yellow viscous mass. The quantitative HPLC of reaction mass shows theoretical yield of 68%. This mass was purified by preparative HPLC (MeOH (65%): ACN (15%): H$_2$O (20%)) to obtain desired product in about 70% purity. Further purification was done by combiflash (0-40% EtOAc in Hexane) to get 42-O-(tetrahydrofuran-3-ol) rapamycin compound having 98.6% purity by HPLC. Then stabilizing agent BHT in acetone was homogeneously mixed with this purified compound and isolation & drying steps were carried out to get white solid powder of 42-O-(tetrahydrofuran-3-ol) rapamycin compound.

REACTION SCHEME-B

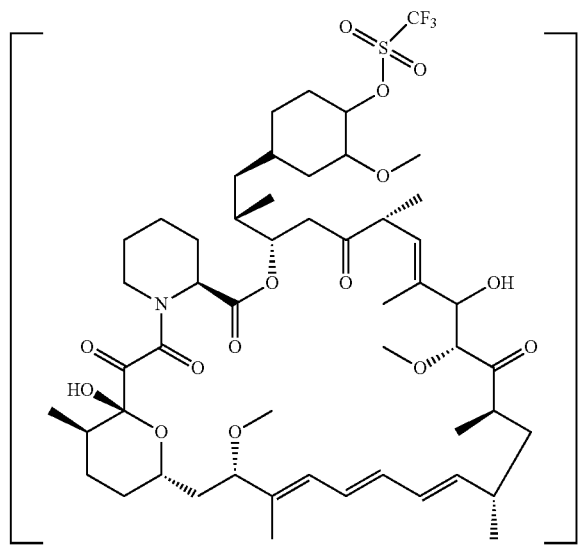

Triflate Intermediate

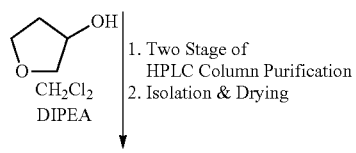

1. Two Stage of HPLC Column Purification
2. Isolation & Drying

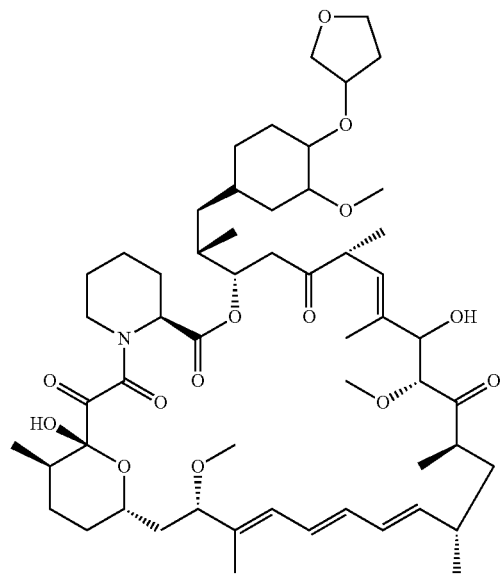

$C_{55}H_{85}NO_{14}$
Mol. Wt.: 984.29
Merilimus-1

The 42-O-(tetrahydrofuran-3-ol) rapamycin compound thus obtained was analytically identified.

Example 1C

STEP 2: Displacement of the Leaving Group with 4 Membered 3-Hydroxy Heteroalkoxyalkyl Compound to Synthesize 42-O-(Heteroalkoxyalkyl) Rapamycin Compound Preparation of 42-O-(oxetan-3-yl) rapamycin (Merilimus 2)

A reaction flask containing triflate intermediate of step-1 was again cooled to −30° C. temperature and 5.94 grams (46 mmol) of N,N-Di-isopropylethylamine (DIPEA) followed by 1.25 grams (13.8 mmol) of Oxetan-3-ol compound in methylene chloride were added. The reaction mixture was stirred at 0° C. temperature for 12 hours. The reaction mixture was then allowed to warm to 25° C. temperature and continuously stirred for 48 hours.

The reaction mixture was further concentrated by evaporation under reduced pressure to provide a pale yellow viscous mass. The quantitative HPLC of reaction mass shows theoretical yield of 71%. This mass was purified by preparative HPLC (MeOH (65%): ACN (15%): $H_2O$ (20%)) method to obtain desired product in about 75% purity. Further purification was done by combiflash (0-40% EtOAc in Hexane) to get 42-O-(oxatane-3-yl) rapamycin compound having 97.7% purity by HPLC. Then stabilizing agent BHT in acetone was homogeneously mixed with purified compound and isolation & drying steps were carried out to get white solid powder of 42-O-(oxatane-3-yl) rapamycin compound.

REACTION SCHEME-C

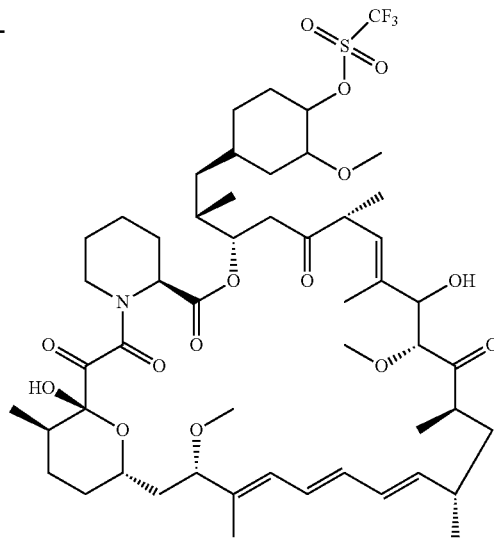

Triflate Intermediate

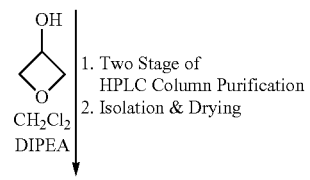

1. Two Stage of HPLC Column Purification
2. Isolation & Drying

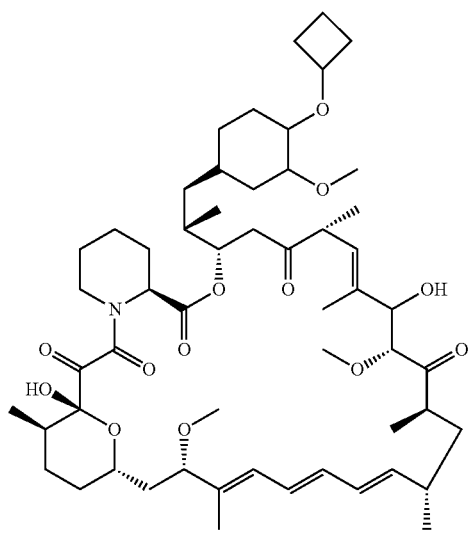

C₅₄H₈₃NO₁₄
Mol. Wt.: 970.26
Merilimus-2

The 42-O-(oxatan-3-yl) rapamycin compound thus obtained was analytically identified.

Example 1D

STEP 2: Displacement of the Leaving Group with 6 Membered 3-Hydroxyheteroalkoxyalkyl Compounds for the Synthesis of 42-O-(Heteroalkoxyalkyl) Rapamycin Compound Preparation of 42-O-(tetrahydropyran-3-yl), rapamycin (Merilimus 3)

A reaction flask containing triflate intermediate of step-1 was further cooled to −50° C. temperature and 6.07 grams (46 mmol) of N,N-di-n-butylethylamine (DNBEA) followed by 1.17 grams (13.8 mmol) of tetrahydropyran-3-ol compound in methylene chloride were added. The reaction mixture was stirred at −10° C. temperature for 12 hours. The reaction mixture was then allowed to warm to 15° C. temperature and continuously stirred for 48 hours.

The reaction mixture was further concentrated by evaporation under reduced pressure to provide a pale yellow viscous mass. The quantitative HPLC of reaction mass shows theoretical yield of 62%. This mass was purified by preparative HPLC (MeOH (65%): ACN (15%): H₂O (20%)) to obtain the desired product in about 65% purity. Further purification was done by combiflash (0-40% EtOAc in Hexane) to get 42-O-(tetrahydropyran-3-yl) rapamycin compound having 97.3% purity by HPLC. Then stabilizing agent BHT in acetone was homogeneously mixed with purified compound and isolation & drying steps were carried out to get white solid powder of 42-O-(tetrahydropyran-3-yl) rapamycin compound.

REACTION SCHEME-D

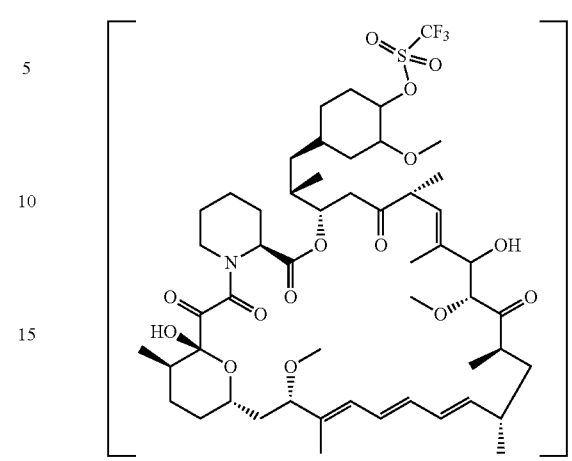

Triflate Intermediate

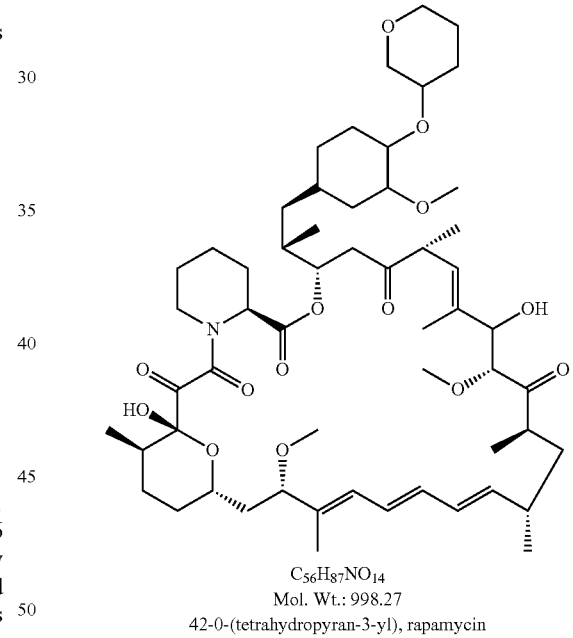

C₅₆H₈₇NO₁₄
Mol. Wt.: 998.27
42-O-(tetrahydropyran-3-yl), rapamycin

The 42-O-(tetrahydropyran-3-yl) rapamycin compound thus obtained was analytically identified.

Similarly, other 42-O-(heteroalkoxyalkyl) rapamycin compounds of formulas (9), (10), (11), (14) and (15) were prepared by treating the triflate intermediate of step 1 with corresponding 3-hydroxy heteroalkoxyalkyl compound by employing the reaction procedure described in Step-2 of Example 1.

Characterization of 42-O-(Heteroalkoxyalkyl) Rapamycin Compounds

42-O-(heteroalkoxyalkyl) rapamycin compounds obtained from four successive batches gave the following values on repeated analyses.

HPLC:

To check the purity of the 42-O-(heteroalkoxyalkyl) rapamycin compounds the following condition was followed by using High Performance Liquid Chromatography, Phenomenex Synergi Hydro-RP 80a (250×4.6 ) mm, 4 micron column. The mobile phase was 65:15:20 methanol:acetonitile:water mixture. The detector was set at 276 nm and the flow rate was adjusted to 1.5 mL/min. Column temperature was 40° C. 2.0 µg of 42-O-(heteroalkoxyalkyl) rapamycin compounds was injected onto the column in a volume of 5.0 µL methanol with run time of 50 min.

Purity for 42-O-(tetrahydrofuran-3-yl), rapamycin (Merilimus-1) compound, 42-O-(oxatan-3-yl), rapamycin (Merilimus-2) compounds and 42-O-(tetrahydropyran-3-yl), rapamycin (Merilimus-3) compound were measured as 98.54%, 97.21% and 97.34% respectively (average of three runs; SD=0.2).

TABLE 1

Chromatography method for measuring purity

| | |
|---|---|
| Column | Phenomenex Synergi Hydro-RP 80a (250 × 4.6) mm, 4 micron column |
| Eluent | 65:15:20 methanol:acetonitile:water mixture (by volume) |
| Flow | 1.5 mL/min |
| Detection | 276 nm |
| Column Temp. | 40° C. |
| Sample Vol. | 2.0 µg injected in a 5.0 µL methanol |
| Run Time | 50 min |

Spectral Studies:

The $^1$HNMR studies are conducted for the starting material rapamycin and its heteroalkoxyalkyl compounds. On comparison, it is found that there are additional proton peaks corresponding to heteroalkoxyalkyl compounds clearly identified and the studies of few compounds of 42-O-(heteroalkoxyalkyl) rapamycin are discussed below.

1) 42-O-(tetrahydrofuran-3-yl), rapamycin (Merilimus-1) compound

I) The protons at 4.3 ppm which corresponds to one proton (tetrahydrofuran ring) attached to oxygen of rapamycin.

C-42-Rapamycin derivative

II) The other two methylene ether linked protons (4 protons) identified at around 3.7 to 3.9 ppm.

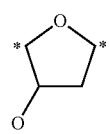

C-42-Rapamycin derivative

III) The methylene 2 protons are identified at around 1.7 ppm (merged with other peaks).

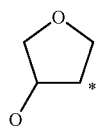

C-42-Rapamycin derivative

The above mentioned (point I, II & III) H-NMR data clearly shows the tetrahydrofuran ring is attached to the rapamycin. The rest of the peaks are identical to rapamycin.

2) 42-O-(oxatan-3-yl), rapamycin (Merilimus-2) compound

I) The protons at 4.3 ppm which corresponds to one proton (oxatan ring) attached to oxygen of rapamycin.

C-42-Rapamycin derivative

II) The other two methylene ether linked protons (4 protons) identified at around 3.6 to 3.8 ppm.

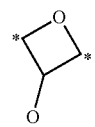

C-42-Rapamycin derivative

The above mentioned (point I & II) H-NMR data clearly shows the oxatan ring is attached to the rapamycin. The rest of the peaks are identical to rapamycin.

3) 42-O-(tetrahydropyran-3-yl), rapamycin (Merilimus-3) compound

I) The protons at 4.3 ppm which corresponds to one proton (tetrahydropyran ring) attached to oxygen of rapamycin.

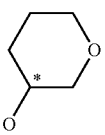

C-42-Rapamycin derivative

II) The other two methylene ether linked protons (4 protons,) identified at around 3.5 to 3.7 ppm.

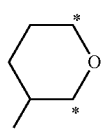

C-42-Rapamycin derivative

III) The two methylene 4 protons are identified at around 1.7 to 2.0 ppm (merged with other peaks).

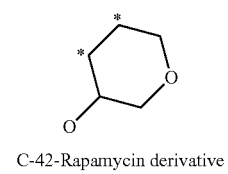

C-42-Rapamycin derivative

The above mentioned (point I, II & III) H-NMR data clearly shows the tetrahydropyran ring is attached to the rapamycin. The rest of the peaks are identical to rapamycin.

The various chemical structures of 42-O-(heteroalkoxyalkyl) rapamycin compounds are further verified by LC Mass Spectrometric ION TRAP analysis. The results are consistent with all the chemical structures of 42-O-(heteroalkoxyalkyl) rapamycin compounds.

The m/z peaks for 42-O-(tetrahydrofuran-3-yl), rapamycin (Merilimus-1, $C_{55}H_{85}NO_{14}$) compound, 42-O-(oxatan-3-yl), rapamycin (Merilimus-2, $C_{54}H_{83}NO_{14}$) compound and 42-O-(tetrahydropyran-3-yl), rapamycin (Merilimus-3, $C_{56}H_{87}NO_{14}$) compound are observed at 984.13, 970.20 and 998.18 respectively; which further confirmed the structure of 42-O-(heteroalkoxyalkyl) rapamycin compounds of the present invention.

Example 2

Stability Analysis of Various 42-O-(heteroalkoxyalkyl) Rapamycin Compounds

All the 42-O-(heteroalkoxyalkyl) rapamycin compounds prepared by this method are unstable and hence decreases their purity over a time period. The purity loss was higher at increased temperature, but there was no apparent change in the impurity profile. Table 2A presents the purity of various 42-O-(heteroalkoxyalkyl) rapamycin compounds at different time intervals and temperature conditions. Examples describe that even in a sealed container at 25° C. temperature, purity of 42-O-(tetrahydrofuran-3-yl) rapamycin (Merilimus-1) compound decreases from 98.7% to 94.1% over a period of 12 weeks, for 42-O-(oxetan-3-yl) rapamycin (Merilimus-2) compound decreases from 97.6% to 93.9% and for 42-O-(tetrahydropyran-3-yl) rapamycin (Merilimus-3) compound decreases from 97.6% to 93.5% over a period of 12 weeks. These losses of purity were increased in a sealed container when held at 40° C. versus kept at 25° C. temperature from 98.6% to 93.5% for Merilimus-1, from 97.3% to 92.7% for Merilimus-2 and from 97.5% to 91.6% for Merilimus-3 over just 12 weeks.

The inventors have also conducted the stability study of various 42-O-(heteroalkoxyalkyl) rapamycin compounds as mentioned above using various BHT concentrations. The study was conducted at 40° C. temperature in sealed container for 8 weeks.

42-O-(heteroalkoxyalkyl) rapamycin compounds obtained as per procedure described in Example 1 are respectively added with anti-oxidant, namely Butylated Hydroxytoluene (or BHT), at a concentration of 0.1%, 0.2%, 0.5%, and 1.0% (w/w) based on 100% (w/w) of 42-O-(heteroalkoxyalkyl) rapamycin compounds in sealed container to study the stability at 40° C. temperature. Study outcome with various concentrations of BHT in Merilimus-1 and Merilimus-2 reveals that the loss in purity was significantly less i.e. 98.3% and 97.4% respectively even after eight-weeks of storage. But in case of 42-O-(tetrahydropyran-3-yl) rapamycin (Merilimus-3) compound the stability drastically reduced to 94.9% even at 1.0% BHT concentration. Comparatively, a control test is provided by adding 0.0% of anti-oxidant (BHT) into 42-O-(tetrahydrofuran-3-yl) rapamycin (Merilimus-1) compound, 42-O-(oxetan-3-yl) rapamycin (Merilimus-2) compound and 42-O-(tetrahydropyran-3-yl) rapamycin (Merilimus-3) compound resulting in a reduction of purity to 94.7%, 93.6% and 92.3% respectively after eight-weeks of storage. The purity data with the addition of different amounts of anti-oxidant as added to 42-O-(tetrahydrofuran-3-yl) rapamycin compound, 42-O-(oxetan-3-yl) rapamycin compound and 42-O-(tetrahydropyran-3-yl) rapamycin compound checked at different time intervals are summarized in Table 2B as below mentioned.

TABLE 2A

Stability data of 42-O-(heteroalkoxyalkyl) rapamycin compounds without BHT at various temperatures

| Time after Synthesis, weeks | 5° C. (sealed) | 25° C. (sealed) | 25° C. (unsealed) | 40° C. (sealed) |
|---|---|---|---|---|
| Purity (%) of 42-O-(tetrahydrofuran-3-yl) rapamycin | | | | |
| 00 | 98.6 | 98.7 | 98.4 | 98.6 |
| 02 | 97.8 | 97.6 | 97.1 | 96.7 |
| 04 | 97.0 | 96.9 | 96.7 | 96.3 |
| 08 | 96.7 | 96.7 | 95.2 | 94.7 |
| 12 | 96.3 | 94.1 | 93.6 | 93.5 |
| Purity (%) of 42-O-(oxetan-3-yl) rapamycin | | | | |
| 00 | 97.7 | 97.6 | 97.3 | 97.3 |
| 02 | 96.5 | 96.2 | 95.9 | 95.5 |
| 04 | 95.6 | 95.1 | 94.8 | 94.6 |
| 08 | 94.8 | 94.5 | 94.0 | 93.6 |
| 12 | 94.2 | 93.9 | 93.6 | 92.7 |
| Purity (%) of 42-O-(tetrahydropyran-3-yl) rapamycin | | | | |
| 00 | 97.3 | 97.6 | 97.0 | 97.5 |
| 02 | 96.0 | 95.7 | 95.3 | 94.4 |
| 04 | 95.4 | 95.2 | 94.5 | 93.7 |
| 08 | 94.5 | 94.6 | 93.8 | 92.3 |
| 12 | 93.9 | 93.5 | 93.1 | 91.6 |

TABLE 2B

Stability results of 42-O-(heteroalkoxyalkyl) rapamycin compounds with various concentration of BHT at 40° C. temperature.

| BHT (w/w) | 0 week | 2 weeks | 4 weeks | 8 weeks |
|---|---|---|---|---|
| Purity (%) of 42-O-(tetrahydrofuran-3-yl) rapamycin | | | | |
| 0.0% | 98.6 | 96.7 | 96.3 | 94.7 |
| 0.1% | 98.6 | 98.5 | 98.5 | 98.4 |
| 0.2% | 98.5 | 98.5 | 98.5 | 98.4 |
| 0.5% | 98.5 | 98.4 | 98.4 | 98.3 |
| 1.0% | 98.5 | 98.4 | 98.4 | 98.3 |
| Purity (%) of 42-O-(oxetan-3-yl) rapamycin | | | | |
| 0.0% | 97.3 | 95.5 | 94.6 | 93.6 |
| 0.1% | 97.7 | 97.5 | 97.5 | 97.5 |
| 0.2% | 97.6 | 97.6 | 97.5 | 97.5 |
| 0.5% | 97.6 | 97.5 | 97.4 | 97.4 |
| 1.0% | 97.6 | 97.5 | 97.4 | 97.4 |
| Purity (%) of 42-O-(tetrahydropyran-3-yl) rapamycin | | | | |
| 0.0% | 97.5 | 94.4 | 93.7 | 92.3 |
| 0.1% | 97.5 | 95.9 | 94.3 | 93.6 |
| 0.2% | 97.6 | 96.3 | 95.6 | 94.1 |
| 0.5% | 97.3 | 96.5 | 95.9 | 94.5 |
| 1.0% | 97.4 | 96.6 | 95.6 | 94.9 |

Figure 2A:
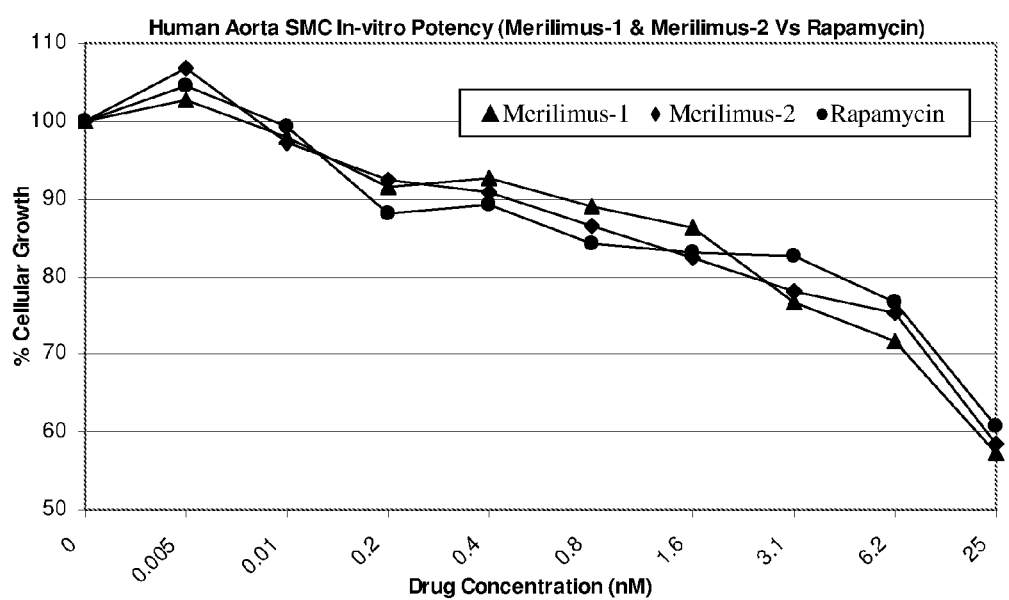
FIG. 2A shows a plot showing in-vitro cellular proliferation assay of human smooth muscle cells in-vitro, expressed as the percentage of growth relative to control cells, as a function of molar drug concentration of 42-O-(Oxetan-3-yl) rapamycin and 42-O-(tetrahydrofuran-3-yl) rapamycin compounds.
Figure 2B:
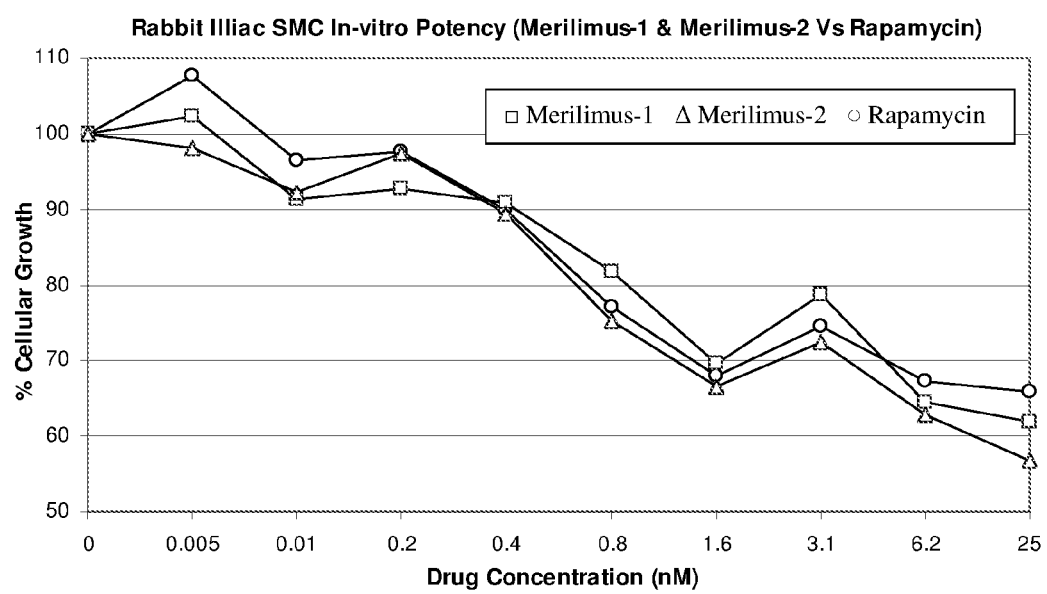
FIG. 2B shows a plot showing in-vitro cellular proliferation of Rabbit Illiac smooth muscle cells in-vitro, expressed as the percentage of growth relative to control cells, as a function of molar drug concentration of 42-O-(oxetan-3-yl) rapamycin and 42-O-(tetrahydrofuran-3-yl) rapamycin Compounds.

The various stability study results indicated that steric hindrance plays a significant role in the stability of 42-O-(heteroalkoxyalkyl) rapamycin compounds. Comparing stability study outcome data of various 4-membered, 5-membered and 6-membered 42-O-(heteroalkoxyalkyl) rapamycin compounds the effect of steric hindrance reverses the order of stability towards the 6-membered group and bulky molecule compounds. The stability data up to 8 weeks for all 42-O-(heteroalkoxyalkyl) rapamycin compounds including Merilimus-1, Merilimus-2 and Merilimus-3 without BHT and with 1.0% BHT at 40° C. temperature are shown in FIGS. 2A and 2B respectively.

Thus these finding gives useful details on importance of antioxidant in maintaining the stability of 42-O-(heteroalkoxyalkyl) rapamycin compounds and further selection of more thermally stable 42-O-(tetrahydrofuran-3-yl) rapamycin (Merilimus-1) compound and 42-O-(oxetan-3-yl) rapamycin (Merilimus-2) compound for designing of biocompatibility test and anti-proliferative study.

Example 3

In-vitro Biocompatibility Tests of 42-O-(Tetrahydrofuran-3-yl) Rapamycin and 42-O-(Oxetan-3-yl) Rapamycin Compounds 3a. Cytotoxicity Test In-vitro assessment was done to check the cytotoxic or necrotic potential of the 42-O-(tetrahydrofuran-3-yl) rapamycin and 42-O-(oxetan-3-yl) rapamycin compounds by extraction method. In this study extracts of test substance were kept in contact with a multiple culture of L-929 (ATCC cell lines CCL-1, NCTC clone 929) *Mus musculus* mouse fibroblast cells for 48 hours. The cells were examined microscopically to assess the changes for its general morphology, vacuolization, detachment, cell lysis and membrane integrity. The test results are shown in Table 3a.

TABLE 3a

| Sample | Observation | Grade | Inference |
|---|---|---|---|
| Positive Control | Cells were rounded off their appendages were withdrawn. Nearly complete destruction of the cell layers. | 3 | Severely Cytotoxic |
| Negative Control | Cells were well in shape and morphology with no cell lysis. | 0 | Non-Cytotoxic |
| Test Sample | Cells were well in shape and morphology with no cell lysis. | 0 | Non-Cytotoxic |

On the basis of cytotoxicity test findings the 42-O-(tetrahydrofuran-3-yl) rapamycin (Merilimus-1) compound and 42-O-(oxetan-3-yl) rapamycin (Merilimus-2) compound did not reveal any toxic effect on cells and both 42-O-(tetrahydrofuran-3-yl) rapamycin and 42-O-(oxetan-3-yl) rapamycin compounds met the requirement of the in-vitro cytotoxicity test.

3b. Haemolysis Test

Haemolysis test was conducted on rabbit blood by in-vitro method to check the haemolytic effect of 42-O-(tetrahydrofuran-3-yl) rapamycin (Merilimus-1) compound and 42-O-(oxetan-3-yl) rapamycin (Merilimus-2) compound. In this study the extracts of the test substances in triplicate were kept in contact with rabbit blood and incubated for 4 hrs. The concentration of plasma haemoglobin liberated in supernatant was calculated by comparing with absorbance of the standard solution in a spectrophotometer at 540 nm. The haemolytic index was calculated by the standard formula and test results are summarised in Table 3b.

TABLE 3b

Haemoglobin Content in Supernatants

| | (Merilimus-1) | | (Merilimus-2) | |
|---|---|---|---|---|
| Sample No. | Haemoglobin (mg/mL) | Haemolytic Index | Haemoglobin (mg/mL) | Haemolytic Index |
| Test (Extract) 1 | 0.34 | 1.7 | 0.40 | 2.0 |
| Test (Extract) 2 | 0.39 | 1.9 | 0.39 | 1.9 |
| Test (Extract) 3 | 0.28 | 1.4 | 0.39 | 1.9 |
| Mean ± S. D. | 0.34 ± 0.05 | 1.7 ± 0.02 | 0.39 ± 0.05 | 1.9 ± 0.02 |

Haemolytic index = Haemoglobin released (mg/ml)/Haemoglobin present (mg/ml) × 100

The Haemolytic index out come was 1.7 for 42-O-(tetrahydrofuran-3-yl) rapamycin compound and 1.9 for 42-O-(oxetan-3-yl) rapamycin compound extracts.

On the basis of haemolytic index results the 42-O-(tetrahydrofuran-3-yl) rapamycin compound and 42-O-(oxetan-3-yl) rapamycin compound show non-haemolytic natures and meet the requirement of the haemolysis test.

3c. Haemocompatibility Test

Haemocompatibility test is conducted to evaluate biological safety of the blood contacting 42-O-(tetrahydrofuran-3-ol) rapamycin and 42-O-(oxetan-3-yl) rapamycin compounds for the medical device. The interaction of test substance with rabbit blood was checked for thrombosis, coagulation, platelet count and leucocyte count. The test results are shown in Table 3c and 3d.

TABLE 3c

Haematological Findings for 42-O-(tetrahydrofuran-3-yl) rapamycin compound

| | | Control Rabbit No. | | | Test Rabbit No. | | | Normal |
|---|---|---|---|---|---|---|---|---|
| S. No. | Parameters | 1 | 2 | 3 | 1 | 2 | 3 | Range |
| 1. | Thrombosis | Nil | Nil | Nil | Nil | Nil | Nil | Normal distribution No aggregation. |
| 2. | Coagulation (PTT in sec.) | 36 | 35 | 38 | 36 | 36 | 39 | 15.7-42.7 |
| 3. | Platelet count | 4.9 | 4.5 | 4.5 | 4.9 | 4.6 | 4.5 | 2.7-6.3 |

TABLE 3c-continued

Haematological Findings for 42-O-(tetrahydrofuran-3-yl) rapamycin compound

| | | Control Rabbit No. | | | Test Rabbit No. | | | Normal |
|---|---|---|---|---|---|---|---|---|
| S. No. | Parameters | 1 | 2 | 3 | 1 | 2 | 3 | Range |
| 4(a) | (in lakhs/cmm) Leucocyte count (in Thousand/cmm) | 7.4 | 6.9 | 7.2 | 7.3 | 6.8 | 7.4 | 5.2-12.5 |
| (b) | Differential | | | | | | | |
| | Neutrophil % | 55 | 49 | 45 | 55 | 47 | 48 | 20-75 |
| | Lymphocyte % | 42 | 48 | 52 | 43 | 50 | 50 | 30-85 |
| | Eosinophil % | 01 | 02 | 02 | 01 | 01 | 01 | 1-4 |
| | Monocyte % | 02 | 01 | 01 | 01 | 02 | 01 | 1-4 |
| | Basophile % | 00 | 00 | 00 | 00 | 00 | 00 | |
| 5. | Distribution of cells | | | | | | | |
| (a) | RBC | Normal | Normal | Normal | Normal | Normal | Normal | |
| (b) | WBC | Normal | Normal | Normal | Normal | Normal | Normal | |
| (c) | Platelets | Normal | Normal | Normal | Normal | Normal | Normal | |

TABLE 3d

Haematological Findings for 42-O-(oxetan-3-yl) rapamycin compound

| | | Control Rabbit No. | | | Test Rabbit No. | | | Normal |
|---|---|---|---|---|---|---|---|---|
| S. No. | Parameters | 1 | 2 | 3 | 1 | 2 | 3 | Range |
| 1. | Thrombosis | Nil | Nil | Nil | Nil | Nil | Nil | Normal distribution No aggregation. |
| 2. | Coagulation (PTT in sec.) | 36 | 35 | 38 | 36 | 36 | 38 | 15.7-42.7 |
| 3. | Platelet count (in lakhs/cmm) | 4.9 | 4.5 | 4.5 | 4.9 | 4.5 | 4.5 | 2.7-6.3 |
| 4(a) | Leucocyte count (in Thousand/cmm) | 7.4 | 6.9 | 7.2 | 7.5 | 6.5 | 7.5 | 5.2-12.5 |
| (b) | Differential | | | | | | | |
| | Neutrophil % | 55 | 49 | 45 | 55 | 48 | 48 | 20-75 |
| | Lymphocyte % | 42 | 48 | 52 | 44 | 50 | 49 | 30-85 |
| | Eosinophil % | 01 | 02 | 02 | 02 | 01 | 02 | 1-4 |
| | Monocyte % | 02 | 01 | 01 | 01 | 01 | 01 | 1-4 |
| | Basophile % | 00 | 00 | 00 | 00 | 00 | 00 | |
| 5. | Distribution of cells | | | | | | | |
| (a) | RBC | Normal | Normal | Normal | Normal | Normal | Normal | |
| (b) | WBC | Normal | Normal | Normal | Normal | Normal | Normal | |
| (c) | Platelets | Normal | Normal | Normal | Normal | Normal | Normal | |

On the basis of the above all haematological findings for 42-O-(tetrahydrofuran-3-yl) rapamycin and 42-O-(oxetan-3-yl) rapamycin compounds did not reveal any significant changes when compared to their corresponding control, as all the parameter fell within the range of normal limit. So the both the compounds 42-O-(tetrahydrofuran-3-yl) rapamycin and 42-O-(oxetan-3-yl) rapamycin compounds are haemocompatible and meet the requirement of the haemocompatibility test.

Example 4

In-vitro Potency of 42-O-(Oxetan-3-yl) Rapamycin and 42-O-(Tetrahydrofuran-3-yl) Rapamycin Compounds In-vitro assessment of relative anti-proliferative effect of novel mTOR inhibitors 42-O-(oxetan-3-yl) rapamycin compound and 42-O-(tetrahydrofuran-3-yl) rapamycin compound with rapamycin was done on human and rabbit smooth muscle cell culture models. In which, human aorta and rabbit illiac artery smooth muscle cell cultures were subjected to increasing doses of 42-O-(oxetan-3-yl) rapamycin compound 42-O-(tetrahydrofuran-3-yl) rapamycin compound and rapamycin over 5 orders of magnitude concentration in the cell culture medium. The ability of the cell culture to reproduce was assessed after drug exposure by addition of a BromodeoxyUridine (BrdU) coloured reagent which causes a colour change in the surviving cells. The extent of colour development was quantified at 450 nm wavelength using a spectrophotometer microplate reader (BMG Labtech, FLUOstar OPTIMA). Higher OD readings reflect an increased incorporation of BrdU into cellular DNA and therefore reflect more active proliferation. On the contrary, lower OD values reflect less incorporation on BrdU and a shift towards cell inhibition. Growth inhibition was calculated by subtracting positive control OD values, which represent 100% uninhibited growth.

The potency of 42-O-(oxetan-3-yl) rapamycin and 42-O-(tetrahydrofuran-3-yl) rapamycin compounds were tested in vitro and compared to the potency of rapamycin. The values of test results are shown in FIG. 3A and FIG. 3B.

The results summary illustrate that the 42-O-(oxetan-3-yl) rapamycin (Merilimus-2) compound and 42-O-(tetrahydrofuran-3-yl) rapamycin (Merilimus-1) compound have similar potency in growth suppression of both hAoSMCs and RbI-ASMCs smooth muscle cells over 5 orders of magnitude concentration. It was also observed that 42-O-(oxetan-3-yl) rapamycin and 42-O-(tetrahydrofuran-3-yl) rapamycin compounds of the present invention more effectively inhibited growth of smooth muscle cells than rapamycin.

Example 5

Formulation using mixture of biodegradable polymers as substrate 80 mg Poly L- lactide, 23 mg Poly (lactide-co-glycolide) and 59 mg 42-O-(tetrahydrofuran-3-yl) rapamycin (Merilimus-1) are dissolved in 50 ml of methylene dichloride solvent to get clear transparent solution. The solution is then spray coated on to medical device surface. A top protective layer of quick release polymer like polyvinyl pyrollidone may be optionally provided. The solvent may then be removed under vacuum.

Example 6

Formulation using lipid as substrate 70 mg hydrogenated castor oil and 47 mg 42-O-(tetrahydrofuran-3-yl) rapamycin (Merilimus-1) are dissolved in 50 ml of methylene dichloride solvent. This clear transparent solution is then spray coated on to medical device surface. A top protective layer of quick release polymer like polyvinyl pyrollidone may be optionally provided. The solvent may then be removed under vacuum.

Example 7

Formulation using mixture of biodegradable polymers nanoparticles as substrate 800 mg Poly L-Lactide, 300 mg Poly (Lactide-co-Glycolide) and 250 mg 42-O-(tetrahydrofuran-3-yl) rapamycin (Merilimus-1) are dissolved in 25 ml of methylene chloride. This solution is then gradually added in to 150 ml aqueous solution of 650 mg Sodium Oleate and 250 mg Vitamin E-TPGS under high speed stirring. This results into a stable suspension. The particle size is reduced further by giving multiple passes through High Pressure Homogenizer. The particle size obtained was between 50 and 250 nm.

Example 8

Formulation using substrate of solid lipid nanoparticles 900 mg hydrogenated castor oil and 225 mg 42-O-(tetrahydrofuran-3-yl) rapamycin (Merilimus-1) are dissolved in 15ml of methylene dichloride. This solution is then gradually added to 150 ml aqueous solution of 500 mg Poloxamer-188 and 150 mg Vitamin E-TPGS under high speed stirring. This resulted into a stable solid drug-lipid suspension. The desired range of particle size was achieved by giving multiple passes through High Pressure Homogenizer. The particle size obtained was between 50 and 450 nm.

Similarly, pharmaceutical compositions for 42-O-(oxetan-3-yl) rapamycin (Merilimus-2) are prepared as described in Example 5, 6, 7 and 8.

We claim:
1. A rapamycin derivative of structural formula 1:

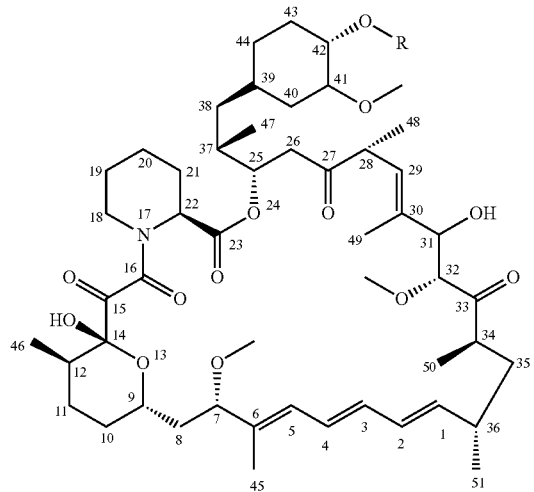

wherein R is a heterocyclic substituent selected from the group consisting of:

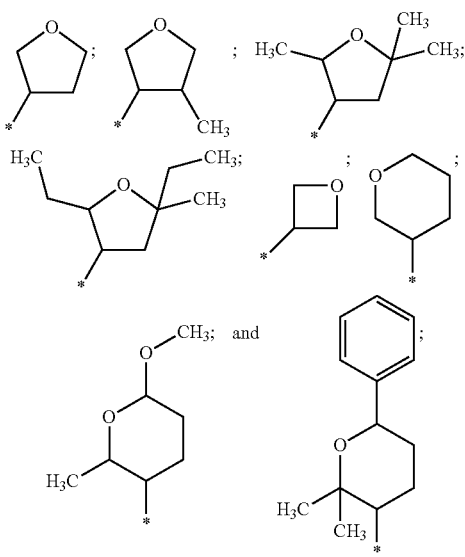

wherein * represents a point of attachment to oxygen.

2. A rapamycin derivative wherein said rapamycin derivative is selected from the group consisting of:
  42-O-(tetrahydrofuran-3-yl) rapamycin (Merilimus-1);
  42-O-(oxetan-3-yl) rapamycin (Merilimus-2);
  42-O-(tetrahydropyran-3-yl) rapamycin (Merilimus-3);
  42-O-(4-methyl, tetrahydrofuran-3-yl) rapamycin;
  42-O-(2,5,5-trimethyl, tetrahydrofuran-3-yl) rapamycin;
  42-O-(2,5-diethyl-2-methyl, tetrahydrofuran-3-yl) rapamycin;
  42-O-(2H-Pyran-3-yl, tetrahydro-6-methoxy-2-methyl) rapamycin and
  42-O-(2H-Pyran-3-yl, tetrahydro-2,2-dimethyl-6-phenyl) rapamycin.

3. The rapamycin derivative according to claim 1 wherein said rapamycin derivative is 42-O-(tetrahydrofuran-3yl) rapamycin (Merilimus-1).

4. The rapamycin derivative according to claim 1 wherein said rapamycin derivative is 42-O-(oxetan-3-yl) rapamycin (Merilimus-2).

5. The rapamycin derivative according to claim 1, wherein said rapamycin derivative is 42-O-(tetrahydropyran-3-yl) rapamycin (Merilimus-3).

6. A process for preparation of a rapamycin derivative, comprising:
   a) reacting rapamycin with triflic anhydride in presence of an organic base and an inert organic solvent to obtain 42-O-(trifluoromethylsulfonyl) rapamycin; and
   b) reacting the 42-O-(trifluoromethylsulfonyl) rapamycin in situ with a hydroxy compound selected from the group consisting of an optionally substituted tetrahydrofuran-3-ol compound, an optionally substituted oxetan-3-ol compound, and an optionally substituted tetrahydropyran-3-ol compound;
   said reaction of the triflate intermediate being carried out in the presence of a trialkyl amine and a halogenated organic solvent to obtain the rapamycin derivative.

7. A process for preparation of the rapamycin derivative according to claim 1, comprising:
   a) reacting rapamycin with triflic anhydride in presence of an organic base and an inert organic solvent to obtain a triflate intermediate; and
   b) reacting the triflate intermediate in situ with a hydroxy compound selected from the group consisting of Tetrahydrofuran-3-ol, Oxetan-3-ol, Tetrahydropyran-3-ol, Tetrahydro-4-methyl furan-3-ol, Tetrahydro-2,5,5-trimethyl furan-3-ol, Tetrahydro-2,5-diethyl-2-methyl furan-3-ol, Tetrahydro-6-methoxy-2-methyl 2H-Pyran-3-ol and Tetrahydro-2,2-dimethyl-6-phenyl 2H-Pyran-3-ol;
   said reaction of the triflate intermediate being carried out in the presence of a trialkyl amine and a halogenated organic solvent to obtain the rapamycin derivative.

8. The process according to claim 7, wherein the organic base is selected from the group consisting of pyridine and its derivatives, and is used in an amount of 3 to 15 mol per mol of rapamycin.

9. The process according to claim 7, wherein said triflic anhydride is used in an amount of 1 to 10 mol per mol of rapamycin to obtain the triflate intermediate.

10. The process according to claim 7, wherein the inert organic solvent is a halogenated organic solvent and is used in an amount of 10 to 30 parts by weight for 1 part by weight of rapamycin.

11. The process according to claim 7 wherein the trialkyl amine is N,N-Di-isopropylethylamine or N,N-Di-n-butyl-ethylamine and is used in the reaction in an amount of 5 to 20 mol per mol of rapamycin.

12. The process according to claim 7 wherein the amount of hydroxy compound used in the reaction is 1 to 7 mol per mol of rapamycin.

13. The process according to claim 7 further comprising:
   purifying the rapamycin derivative; and
   stabilizing said purified rapamycin derivative by the addition of an anti-oxidant for enhancing a storage stability.

14. The process according to claim 13, wherein the anti-oxidant is selected from the group consisting of Butylated hydroxytoluene (BHT), DL-α-tocopherol, propyl gallate, ascorbyl palmitate, 3-tert-butyl-4-hydroxyanisole, 2-tert-butyl-4-hydroxyanisole, and fumaric acid and is used in an amount of between 0.1% to 1.0% (w/w) based on 100% (w/w) of the rapamycin derivative.

15. A pharmaceutical composition comprising a rapamycin derivative according to claim 1 together with one or more pharmaceutical carriers administrable orally, parenterally, intravascularly, or via a coating on an implantable medical device.

16. The pharmaceutical composition according to claim 15, wherein said implantable medical devices are stent and balloon catheter.

* * * * *